US012797165B2

(12) United States Patent
Saphier et al.

(10) Patent No.: US 12,797,165 B2
(45) Date of Patent: Nov. 17, 2026

(54) INTRAORAL 3D SCANNER CALIBRATION

(71) Applicant: Align Technology, Inc., San Jose, CA (US)

(72) Inventors: Ofer Saphier, Rechovot (IL); Pavel Gorodetsky, Rishon LeZion (IL); Tal Levy, Rehovot (IL); Eddy Pincu, Richon LeZion (IL); Ditza Auerbach, Aseret (IL); Raphael Levy, Jerusalem (IL); Tal Verker, Ofra (IL); Noam Shekel, Kiryat Gat (IL); Eliran Dafna, Beer-sheva (IL)

(73) Assignee: Align Technology, Inc., San Jose, CA (US)

( * ) Notice: Subject to any disclaimer, the term of this patent is extended or adjusted under 35 U.S.C. 154(b) by 204 days.

(21) Appl. No.: 18/537,773

(22) Filed: Dec. 12, 2023

(65) Prior Publication Data

US 2024/0197448 A1 Jun. 20, 2024

Related U.S. Application Data

(60) Provisional application No. 63/433,379, filed on Dec. 16, 2022.

(51) Int. Cl.
*A61C 9/00* (2006.01)
*A61B 1/00* (2006.01)
(Continued)

(52) U.S. Cl.
CPC .......... *A61C 9/006* (2013.01); *A61B 1/00194* (2022.02); *A61B 1/0057* (2013.01); *A61C 9/0053* (2013.01); *G01B 11/25* (2013.01)

(58) Field of Classification Search
CPC ......... G06T 15/506; G06T 15/08; G06T 7/75; G06T 17/00; G06T 2207/30036;
(Continued)

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |

(Continued)

OTHER PUBLICATIONS

T. Treibitz, Y. Schechner, C. Kunz and H. Singh, "Flat Refractive Geometry," in IEEE Transactions on Pattern Analysis and Machine Intelligence, vol. 34, No. 1, pp. 51-65, Jan. 2012, doi: 10.1109/TPAMI.2011.105. (Year: 2012).*

(Continued)

*Primary Examiner* — Stephen R Koziol
*Assistant Examiner* — Samuel D. Baynes
(74) *Attorney, Agent, or Firm* — Lowenstein Sandler LLP

(57) ABSTRACT

An apparatus for intraoral scanning comprises an elongate wand comprising a probe at a distal end of the wand, one or more cameras and a computer processor. The one or more cameras are disposed within the probe and arranged within the probe such that the one or more cameras receive rays of light from an intraoral cavity in a non-central manner, wherein the non-central manner in which the one or more cameras receive the rays of light from the intraoral cavity introduces image distortion. The computer processor is configured to generate a three-dimensional model of an intraoral surface based on images from the one or more cameras, wherein the computer processor compensates for the image distortion specifically introduced by the non-central manner in which the one or more cameras receive the rays of light from the intraoral cavity.

14 Claims, 13 Drawing Sheets

(51) Int. Cl.
*A61B 1/005* (2006.01)
*G01B 11/25* (2006.01)

(58) Field of Classification Search
CPC ...... A61C 9/006; G01J 2001/067; G01J 1/00; H04N 13/221; H04N 13/246
See application file for complete search history.

(56) References Cited

U.S. PATENT DOCUMENTS

| | | | |
|---|---|---|---|
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,698,068 | B2 | 4/2010 | Babayoff |
| 7,916,911 | B2 | 3/2011 | Kaza et al. |
| 8,108,189 | B2 | 1/2012 | Chelnokov et al. |
| 8,244,028 | B2 | 8/2012 | Kuo et al. |
| 8,587,582 | B2 | 11/2013 | Matov et al. |
| 8,948,482 | B2 | 2/2015 | Levin |
| D742,518 | S | 11/2015 | Barak et al. |
| 9,192,305 | B2 | 11/2015 | Levin |
| 9,261,356 | B2 | 2/2016 | Lampert et al. |
| 9,261,358 | B2 | 2/2016 | Atiya et al. |
| 9,299,192 | B2 | 3/2016 | Kopelman |
| D760,901 | S | 7/2016 | Barak et al. |
| 9,393,087 | B2 | 7/2016 | Moalem |
| 9,408,679 | B2 | 8/2016 | Kopelman |
| 9,431,887 | B2 | 8/2016 | Boltanski |
| 9,439,568 | B2 | 9/2016 | Atiya et al. |
| 9,451,873 | B1 | 9/2016 | Kopelman et al. |
| D768,861 | S | 10/2016 | Barak et al. |
| D771,817 | S | 11/2016 | Barak et al. |
| 9,491,863 | B2 | 11/2016 | Boltanski |
| D774,193 | S | 12/2016 | Makmel et al. |
| 9,510,757 | B2 | 12/2016 | Kopelman et al. |
| 9,660,418 | B2 | 5/2017 | Atiya et al. |
| 9,668,829 | B2 | 6/2017 | Kopelman |
| 9,675,430 | B2 | 6/2017 | Verker et al. |
| 9,693,839 | B2 | 7/2017 | Atiya et al. |
| 9,717,402 | B2 | 8/2017 | Lampert et al. |
| 9,724,177 | B2 | 8/2017 | Levin |
| 9,844,426 | B2 | 12/2017 | Atiya et al. |
| 10,076,389 | B2 | 9/2018 | Wu et al. |
| 10,098,714 | B2 | 10/2018 | Kuo |
| 10,108,269 | B2 | 10/2018 | Sabina et al. |
| 10,111,581 | B2 | 10/2018 | Makmel |
| 10,111,714 | B2 | 10/2018 | Kopelman et al. |
| 10,123,706 | B2 | 11/2018 | Elbaz et al. |
| 10,136,972 | B2 | 11/2018 | Sabina et al. |
| 10,380,212 | B2 | 8/2019 | Elbaz et al. |
| 10,390,913 | B2 | 8/2019 | Sabina et al. |
| 10,453,269 | B2 | 10/2019 | Furst |
| 10,456,043 | B2 | 10/2019 | Atiya et al. |
| 10,499,793 | B2 | 12/2019 | Ozerov et al. |
| 10,504,386 | B2 | 12/2019 | Levin et al. |
| 10,507,087 | B2 | 12/2019 | Elbaz et al. |
| 10,517,482 | B2 | 12/2019 | Sato et al. |
| 10,695,150 | B2 | 6/2020 | Kopelman et al. |
| 10,708,574 | B2 | 7/2020 | Furst et al. |
| 10,772,506 | B2 | 9/2020 | Atiya et al. |
| 10,813,727 | B2 | 10/2020 | Sabina et al. |
| 10,888,399 | B2 | 1/2021 | Kopelman et al. |
| 10,952,816 | B2 | 3/2021 | Kopelman |
| 10,980,613 | B2 | 4/2021 | Shanjani et al. |
| 11,013,581 | B2 | 5/2021 | Sabina et al. |
| D925,739 | S | 7/2021 | Shalev et al. |
| 11,096,765 | B2 | 8/2021 | Atiya et al. |
| 11,238,586 | B2 | 2/2022 | Minchenkov et al. |
| 11,367,192 | B2 | 6/2022 | Kopelman et al. |
| 11,455,727 | B2 | 9/2022 | Minchenkov et al. |
| 11,478,132 | B2 | 10/2022 | Kopelman et al. |
| 11,563,929 | B2 | 1/2023 | Saphier et al. |
| 11,633,268 | B2 | 4/2023 | Moalem et al. |
| 11,707,238 | B2 | 7/2023 | Moshe et al. |
| RE49,605 | E | 8/2023 | Kopelman |
| 11,744,681 | B2 | 9/2023 | Kopelman et al. |
| 11,759,277 | B2 | 9/2023 | Shalev et al. |
| 11,896,461 | B2 | 2/2024 | Saphier et al. |
| 2004/0217260 | A1* | 11/2004 | Bernardini .............. G06T 7/521 250/208.1 |
| 2018/0028063 | A1* | 2/2018 | Elbaz .................. G06F 16/9535 |
| 2018/0089855 | A1* | 3/2018 | Rodrigues ............... G06T 7/174 |
| 2020/0404243 | A1* | 12/2020 | Saphier .................. A61C 9/006 |
| 2021/0059796 | A1 | 3/2021 | Weiss et al. |
| 2021/0121049 | A1 | 4/2021 | Rudnitsky et al. |
| 2021/0128281 | A1 | 5/2021 | Peleg |
| 2021/0137653 | A1 | 5/2021 | Saphier et al. |
| 2021/0196152 | A1 | 7/2021 | Saphier et al. |
| 2021/0243369 | A1* | 8/2021 | Dal Mutto ................ G06T 7/80 |

OTHER PUBLICATIONS

Peter A. van Nijnatten, "Mathematical modeling of optical glazing performance," Proc. SPIE 2255, Optical Materials Technology for Energy Efficiency and Solar Energy Conversion XIII, Sep. 9, 1994; https://doi.org/10.1117/12.185417 (Year: 1994).*

Hui-Liang Shen, Yue Cheng "Calibrating light sources by using a planar mirror," Journal of Electronic Imaging 20(1), 013002 (Jan. 1, 2011) https://doi.org/10.1117/1.3533326 (Year: 2011).*

* cited by examiner

INTRAORAL 3D SCANNER CALIBRATION

RELATED APPLICATIONS

This patent application claims the benefit under 35 U.S.C. § 119(e) of U.S. Provisional Application No. 63/433,379, filed Dec. 16, 2022.

FIELD OF THE INVENTION

The present invention relates generally to three-dimensional imaging, and more particularly to intraoral three-dimensional imaging.

BACKGROUND

Digital dental impressions utilize intraoral scanning to generate three-dimensional digital models of an intraoral three-dimensional surface of a subject. Digital intraoral scanners often use structured light three-dimensional imaging. The surface of a subject's teeth may be highly reflective and somewhat translucent, which may reduce the contrast in the structured light pattern reflecting off the teeth.

US 2019/0388193 to Saphier et al., which is assigned to the assignee of the present application and is incorporated herein by reference, describes an apparatus for intraoral scanning including an elongate handheld wand that has a probe. One or more light projectors and two or more cameras are disposed within the probe. The light projectors each have a pattern generating optical element, which may use diffraction or refraction to form a light pattern. Each camera may be configured to focus between 1 mm and 30 mm from a lens that is farthest from the camera sensor. Other applications are also described.

US 2019/0388194 to Atiya et al., which is assigned to the assignee of the present application and is incorporated herein by reference, describes handheld wand including a probe at a distal end of the elongate handheld wand. The probe includes a light projector and a light field camera. The light projector includes a light source and a pattern generator configured to generate a light pattern. The light field camera includes a light field camera sensor, the light field camera sensor includes an image sensor including an array of sensor pixels, and an array of micro-lenses disposed in front of the image sensor such that each micro-lens is disposed over a sub-array of the array of sensor pixels. Other applications are also described.

US 2020/0404243 to Saphier et al., which is assigned to the assignee of the present application and is incorporated herein by reference, describes a method for generating a 3D image, including driving structured light projector(s) to project a pattern of light on an intraoral 3D surface, and driving camera(s) to capture images, each image including at least a portion of the projected pattern, each one of the camera(s) comprising an array of pixels. A processor compares a series of images captured by each camera and determines which of the portions of the projected pattern can be tracked across the images. The processor constructs a three-dimensional model of the intraoral three-dimensional surface based at least in part on the comparison of the series of images. Other embodiments are also described.

SUMMARY OF THE INVENTION

Applications of the present invention include systems and methods related to calibration of the optical system of an intraoral scanner. Typically, the intraoral scanner includes an elongate wand (e.g., an elongate handheld wand) with a probe at a distal end of the wand. The probe has a transparent window through which light rays enter and exit the probe. One or more cameras are disposed within the probe and arranged within the probe such that the one or more cameras receive rays of light from an intraoral cavity in a non-central manner, i.e., the relationship between points in 3D world-coordinate space and corresponding points on the camera sensors of the one or more cameras is described by a set of camera rays for which there is no single point in space through which all of the cameras rays pass (in contrast, for example, to a pinhole camera model). The non-central manner in which the one or more cameras receive the rays of light from the intraoral cavity introduces image distortion in scanned images captured by the intraoral scanner. In order to accurately digitally reconstruct the scanned intraoral surface a computer processor generates a three-dimensional model of the intraoral surface based on the scanned images from the one or more cameras using a reconstruction algorithm that compensates for the image distortion specifically introduced by the non-central manner in which the one or more cameras receive the rays of light from the intraoral cavity, as further described hereinbelow.

For some applications, the compensation for the image distortion specifically introduced by the non-central manner in which the one or more cameras receive the rays of light from the intraoral cavity is performed by analyzing the scanning data, e.g., the scanned images, using camera calibration data indicating a set of camera rays respectively corresponding to points (u,v) on a sensor of the one or more cameras, each of the camera rays having a distinct origin and direction. To generate the camera calibration data, calibration images of a 2D camera calibration target having a plurality of distinct calibration features are captured while the 2D camera calibration target is disposed at a respective plurality of distances, in a given direction z in space. A relationship is modeled between (a) points in 3D space defined by an x,y,z coordinate system and (b) corresponding points (u,v) on a sensor of the one or more cameras, as a set of camera rays using a model in which (x,y) as a function of (u,v) varies linearly with distance along z, further described hereinbelow.

It is known in the field of intraoral scanning to place a sleeve having a transparent sleeve-window over the probe of an intraoral scanner, e.g., for hygienic reasons. For some applications the entire sleeve is transparent such that the sleeve-window refers to the specific area of the transparent sleeve which lines up with the transparent window of the probe when the sleeve is placed over the probe. For some applications, the sleeve itself is not transparent, but has a transparent sleeve-window which lines up with the transparent window of the probe when the sleeve is placed over the probe. The transparent window of the sleeve through which light rays exit and enter the probe during scanning typically changes the overall optical conditions. In order to achieve high-accuracy 3D digital reconstruction of the scanned intraoral surface, the changes in the optical conditions due to the presence of a sleeve are accounted for during a calibration process of the intraoral scanner. The inventors have realized that if the optical changes caused by the addition of a sleeve are known, e.g., by knowing the optical properties of a sleeve-window and how they affect light rays passing through the sleeve-window, then the intraoral scanner may be initially calibrated without the presence of a sleeve, and the calibration data mathematically updated to account for the presence of a sleeve-window. As further described hereinbelow, this reduces the complexity of the physical calibration system and provides the flexibility to generate calibration data for a plurality of different sleeve-windows, each with differing optical properties, all based on initial calibration data acquired without the presence of an additional calibration window representing a sleeve.

For some applications, the intraoral scanner includes an elongate handheld wand used to obtain scanning data of an intraoral surface. The elongate handheld wand includes (i) a probe at a distal end of the handheld wand, the probe having a transparent window, (ii) one or more cameras disposed within the probe and arranged to receive light from the intraoral surface through the transparent window of the probe, and (iii) one or more structured light projectors arranged to project structured light onto the intraoral surface through the transparent window of the probe. Typically, the one or more cameras and the one or more structured light projectors go through an initial calibration during manufacturing in order to obtain initial calibration data. The initial calibration data for the one or more cameras and/or the one or more structured light projectors may be updated mathematically based on a known optical property of a given sleeve-window, as further described hereinbelow. For some applications, during a scan, a computer processor (i) receives the initial calibration data for the one or more cameras and/or the one or more structured light projectors, (ii) receives an indication, e.g., input from a dentist, of the presence of a sleeve-window positioned between the intraoral surface and the transparent window of the probe, and (iii) accesses the updated model of the initial calibration data for the combination of the transparent window of the probe and the sleeve-window.

For some applications, images of the intraoral surface are captured under non-structured light, e.g., broad spectrum light and/or Near Infra-Red (NIR). Typically, the elongate handheld wand of the intraoral scanner includes one or more non-structured illumination sources disposed within the handheld wand. Ideally, in order to capture images of the intraoral surface under non-structured light, the non-structured light should uniformly illuminate the intraoral surface. However, due to the close proximity of the scanned surface to the probe, the illumination from the one or more non-structured light sources is incident on the intraoral surface in a non-uniform manner, i.e., images of the intraoral surface are captured using the one or more cameras under non-uniform illumination from the one or more non-structured illumination sources.

In order to compensate for the non-uniformity of the illumination, for each manufactured intraoral scanner, a mathematical model of the illumination from the specific one or more non-structured illumination sources of the intraoral scanner is calculated and stored as part of the initial calibration data for the intraoral scanner. A computer processor analyzes the images captured by the one or more cameras under the non-uniform illumination from the one or more non-structured illumination sources and compensates for the non-uniformity of the illumination using the calibration data generated based on the mathematical model of the illumination from the specific one or more non-structured illumination sources of the apparatus. For some applications, the mathematical model of the illumination includes the location of each of the one or more non-structured illumination sources as seen in a 3D world-coordinate space by the one or more cameras. For some applications, the mathematical model of the illumination also includes a measure of relative illumination (e.g., vignetting) for each of the one or more cameras, and an estimated illumination intensity-per-angle emitted from each of the one or more non-structured illumination sources.

Alternatively or additionally, for some applications, the computer processor analyzes images captured by the one or more cameras under the non-uniform illumination from the one or more non-structured illumination sources and compensates for the non-uniformity of the illumination using calibration data indicating an amount of light received at each point (u,v) on a sensor of the one or more cameras for different respective distances from the one or more cameras. To generate the calibration data, calibration images are captured, using the one or more cameras, of a 2D calibration target. The capturing of the calibration images is performed while the 2D calibration target is disposed at a respective plurality of distances, in a given direction z in space, from the one or more cameras. A mathematical function is fit to the calibration images corresponding to an amount of light received at each point (u,v) on a sensor of the one or more cameras for each of the respective plurality of distances in the z direction.

Typically, there are a plurality of different types of illumination sources in the intraoral scanner, e.g., structured light projectors utilizing lasers in different colors, broad spectrum LEDs, and NIR LEDs. In order to achieve high accuracy scanning, small deviations in the camera optics for different respective wavelengths, e.g., chromatic aberrations, are accounted for in the initial calibration process of the one or more cameras. Thus, for some applications, the initial calibration of one or more cameras of the intraoral scanner is repeated under illumination from each type of illumination that may be used during scanning. As described hereinabove, to calibrate the one or more cameras a 2D camera calibration target having a plurality of distinct calibration features is used, e.g., a checkerboard pattern with additional unique markings such as letters and numbers. During calibration of the one or more cameras, for each repetition of the calibration the 2D camera calibration target is uniformly backlit with one of the various types of illumination that the one or more cameras may encounter during intraoral scanning, such that the initial camera calibration data includes calibration data for each wavelength the one or more cameras may encounter during intraoral scanning.

For some applications, in order to simplify the calibration system, a single uniform illumination source includes multiple arrays of light emitting diodes (LEDs), each array having one of the various different wavelengths. The LEDs of each of the respective arrays are spaced such that when each of the respective arrays is activated individually, the uniform illumination source uniformly illuminates the 2D camera calibration target. For some applications, the uniform illumination source includes (i) a first array of light emitting diodes (LEDs), each LED of the first array having a first wavelength between 400 and 700 nanometers, (ii) a second array of LEDs interleaved with the first array, each LED of the second array having a second wavelength between 400 and 700 nanometers, the second wavelength distinct from the first wavelength, (iii) a third array of LEDs interleaved with the first and second arrays, each LED of the third array having a third wavelength between 800 and 2500 nanometers, and (iv) a fourth array of LEDs interleaved with the first, second, and third arrays, each LED of the fourth array emitting broadband light.

There is therefore provided, in accordance with some applications of the present invention, apparatus for intraoral scanning, the apparatus including:

an elongate handheld wand including a probe at a distal end of the handheld wand;

one or more cameras disposed within the probe and arranged within the probe such that the one or more cameras receive rays of light from an intraoral cavity in a non-central manner, wherein the non-central manner in which the one or more cameras receive the rays of light from the intraoral cavity introduces image distortion; and a computer processor configured to generate a three-dimensional model of an intraoral surface based on images from the one or more cameras, wherein the computer processor compensates for the image distortion specifically introduced by the non-central manner in which the one or more cameras receive the rays of light from the intraoral cavity.

For some applications, the one or more cameras are rigidly fixed within the probe.

For some applications, the probe includes a transparent window, and the non-central manner in which the one or more cameras receives the rays of light from the intraoral cavity is due to the rays of light passing through the transparent window of the probe.

For some applications, for each of the one or more cameras, an angle between an optical axis of the camera and an axis that is normal to the transparent window is 7-45 degrees.

There is further provided, in accordance with some applications of the present invention, a method for intraoral scanning, the method including:

using an elongate handheld wand to obtain scanning data of an intraoral surface, the elongate handheld wand including:

a probe at a distal end of the handheld wand, and one or more cameras disposed within the probe and arranged within the probe such that the one or more cameras receive rays of light from an intraoral cavity in a non-central manner, wherein the non-central manner in which the one or more cameras receive the rays of light from the intraoral cavity introduces image distortion; and using a computer processor:

compensating for image distortion specifically introduced by the non-central manner in which the one or more cameras receive the rays of light from the intraoral cavity by analyzing the scanning data using camera calibration data generated by:

capturing, using the one or more cameras, calibration images of a 2D camera calibration target having a plurality of distinct calibration features, the capturing of the calibration images performed while the 2D camera calibration target is disposed at a respective plurality of distances, in a given direction z in space, from the one or more cameras, and modeling a relationship between (i) points in 3D space defined by an x,y,z coordinate system and (ii) corresponding points (u,v) on a sensor of the one or more cameras, as a set of camera rays using a model in which x,y as a function of u,v varies linearly with distance along z; and generating a three-dimensional model of an intraoral surface based on the analyzing of the scanning data.

For some applications, modeling the relationship includes modeling the set of rays as a function that takes a given u,v,z and outputs a corresponding x,y, the function in the form of:

$$F(u,v,z)=G1(u,v)+z*G2(u,v)$$

the function describing a camera ray in which G1 (u,v) outputs an x,y corresponding to z=0 and G2(u,v) outputs an x,y corresponding to z=1.

There is further provided, in accordance with some applications of the present invention, apparatus for intraoral scanning, the apparatus including:

an elongate handheld wand configured to obtain scanning data of an intraoral surface, the elongate handheld wand including:

a probe at a distal end of the handheld wand; and one or more cameras disposed within the probe and arranged within the probe such that the one or more cameras receive rays of light from an intraoral cavity in a non-central manner, wherein the non-central manner in which the one or more cameras receive the rays of light from the intraoral cavity introduces image distortion; and a computer processor configured to:

compensate for image distortion specifically introduced by the non-central manner in which the one or more cameras receive the rays of light from the intraoral cavity by analyzing the scanning data using camera calibration data generated by:

capturing, using the one or more cameras, calibration images of a 2D camera calibration target having a plurality of distinct calibration features, the capturing of the calibration images performed while the 2D camera calibration target is disposed at a respective plurality of distances, in a given direction z in space, from the one or more cameras, and modeling a relationship between (i) points in 3D space defined by an x,y,z coordinate system and (ii) corresponding points (u,v) on a sensor of the one or more cameras, as a set of camera rays using a model in which x,y as a function of u,v varies linearly with distance along z; and generate a three-dimensional model of the intraoral surface based on the analyzing of the scanning data.

For some applications, modeling the relationship includes modeling the set of rays as a function that takes a given u,v,z and outputs a corresponding x,y, the function in the form of:

$$F(u, v, z) = G1(u, v) + z * G2(u, v)$$

the function describing a camera ray in which G1(u,v) outputs an x,y corresponding to z=0 and G2(u,v) outputs an x,y corresponding to z=1.

There is further provided, in accordance with some applications of the present invention, a method for intraoral scanning, the method including:

using an elongate handheld wand to obtain scanning data of an intraoral surface, the elongate handheld wand including:

a probe at a distal end of the handheld wand, one or more cameras disposed within the probe and arranged to receive light from the intraoral surface through a transparent window of the probe, and one or more structured light projectors arranged to project structured light onto the intraoral surface through the transparent window of the probe; and using a computer processor:

receiving initial calibration data for one or more devices selected from the group consisting of: (a) the one or more cameras, and (b) the one or more structured light projectors;

receiving an indication of the presence of a sleeve-window positioned between the intraoral surface and the transparent window of the probe; and accessing an updated model of the initial calibration data for the combination of the transparent window of the probe and the sleeve-window, wherein the updated model is calculated from the initial calibration data based on an optical property of the sleeve-window.

For some applications, the optical property of the sleeve window is a thickness of the sleeve-window and the index of refraction of the sleeve window.

For some applications:

the selected device is the one or more cameras, the initial calibration data models a relationship between points in 3D space (x,y,z) and corresponding points (u,v) on a sensor of the one or more cameras as a set of camera rays, each camera ray having an origin and direction, and the updated model of the initial calibration data is calculated by mathematically shifting the origin for each of the camera rays.

For some applications:

the selected device is the one or more structured light projectors, each structured light projector configured to project a plurality of structured light features, each projected structured light feature corresponding to a distinct projector ray, the initial calibration data defines an origin and direction vector for each of the projector rays, and the updated model of the initial calibration data is calculated by mathematically shifting the origin for each of the projector rays.

For some applications:

each structured light projector is configured to project a plurality of structured light features, each projected structured light feature corresponding to a distinct projector ray Rj, and the method further includes, using the computer processor:

receiving projector-ray calibration data indicating, per projector ray Rj, at least one projector-ray parameter selected from the group consisting of:

a shape of the projected structured light feature corresponding to projector ray Rj based on a plurality of calibration images of the projected structured light feature on a calibration target and a known respective angle at which projector ray Rj was incident on the calibration target for each calibration image, and intensity of projector ray Rj based on a plurality of calibration images of the projected structured light feature on a calibration target, receiving scanning data of the intraoral surface, the scanning data including images of a plurality of projected structured light features on the intraoral surface, and running a correspondence algorithm to identify which projected structured light feature on the intraoral surface corresponds to each respective projector ray Rj, using the at least one project-ray parameter per projector ray Rj as an input to the correspondence algorithm.

There is further provided, in accordance with some applications of the present invention, apparatus for intraoral scanning, the apparatus including:

an elongate handheld wand including a probe at a distal end of the handheld wand;

one or more cameras disposed within the probe;

one or more non-structured illumination sources disposed within the handheld wand, and arranged such that images of the intraoral surface are captured using the one or more cameras under non-uniform illumination from the one or more non-structured illumination sources; and a computer processor configured to analyze images captured by the one or more cameras under the non-uniform illumination from the one or more non-structured illumination sources, wherein the computer processor is configured to compensate for the non-uniformity of the illumination using calibration data generated based on a mathematical model of the illumination from the specific one or more non-structured illumination sources of the apparatus, the mathematical model including the location of each of the one or more non-structured illumination sources as seen in a 3D world-coordinate space by the one or more cameras.

For some applications, the computer processor is configured to compensate for the non-uniformity of the illumination using calibration data generated based on the mathematical model of the illumination from the specific one or more non-structured light sources of the apparatus, the mathematical model including the location of each of the one or more non-structured illumination sources as seen in a 3D world-coordinate space by the one or more cameras via images of a reflective calibration target.

For some applications, the computer processor is configured to compensate for the non-uniformity of the illumination using calibration data generated based on the mathematical model of the illumination from the specific one or more non-structured light sources of the apparatus, the mathematical model including the location of each of the one or more non-structured illumination sources as seen in a 3D world-coordinate space by the one or more cameras via images of the reflective calibration target that are acquired prior to the apparatus being packaged for commercial sale.

For some applications, the computer processor is configured to update the mathematical model of the illumination from the specific one or more non-structured light sources of the apparatus after a given use of the handheld wand to scan an intraoral surface of a patient and before a subsequent use of the handheld wand to scan an intraoral surface of a patient.

For some applications, the mathematical model of the illumination from the specific one or more non-structured illumination sources of the apparatus includes an estimated illumination intensity-per-angle emitted from each of the one or more non-structured illumination sources.

For some applications, the estimated illumination intensity-per-angle emitted from each of the one or more non-structured illumination sources is estimated based on calibration images captured using the one or more cameras of a diffusive calibration target illuminated with the one or more non-structured illumination sources.

For some applications, the computer processor is configured to further compensate for the non-uniformity of the illumination of the one or more non-structured illumination sources using calibration data indicative of a measure of relative illumination for each of the one or more cameras. In one embodiment, camera vignette calibration data indicative of a measure of vignetting is used for each of the one or more cameras.

For some applications, the camera-vignette calibration data is generated by:

capturing, using the one or more cameras, calibration images of a 2D calibration target having a plurality of distinct calibration features, the capturing of the calibration images performed while the 2D calibration target is back-lit with uniform illumination, and fitting a vignetting model (or other relative illumination model) to each of the one or more cameras.

For some applications, the mathematical model of the illumination from the specific one or more non-structured illumination sources of the apparatus includes an estimated illumination intensity-per-angle emitted from each of the one or more non-structured illumination sources.

For some applications, the probe has a transparent window through which the one or more non-structured illumination sources are configured to emit light onto an intraoral surface, and the mathematical model includes (i) the distance of a calibration target from the transparent window of the probe and (ii) Fresnel reflections from the transparent window.

For some applications, the one or more non-structured illumination sources include one or more broad spectrum illumination sources.

For some applications, the one or more non-structured illumination sources include one or more Near Infra-Red (NIR) illumination sources.

There is further provided, in accordance with some applications of the present invention, apparatus for intraoral scanning, the apparatus including:

an elongate handheld wand including a probe at a distal end of the handheld wand;

one or more cameras disposed within the probe;

one or more non-structured illumination sources disposed within the handheld wand, and arranged such that images of the intraoral surface are captured using the one or more cameras under non-uniform illumination from the one or more non-structured illumination sources; and a computer processor configured to analyze images captured by the one or more cameras under the non-uniform illumination from the one or more non-structured illumination sources, wherein the computer processor is configured to compensate for the non-uniformity of the illumination using calibration data generated by:

capturing, using the one or more cameras, calibration images of a 2D calibration target, the capturing of the calibration images performed while the 2D calibration target is disposed at a respective plurality of distances, in a given direction z in space, from the one or more cameras, and fitting a mathematical function corresponding to an amount of light received at each point (u,v) on a sensor of the one or more cameras for each of the respective plurality of distances in the z direction.

For some applications, capturing includes capturing calibration images of a solid-color 2D calibration target.

There is further provided, in accordance with some applications of the present invention, apparatus including a uniform illumination source for calibration of one or more cameras disposed within an intraoral scanner, the uniform illumination source configured to illuminate a camera calibration target and including:

a first array of light emitting diodes (LEDs), each LED of the first array having a first wavelength between 400 and 700 nanometers;

a second array of LEDs interleaved with the first array, each LED of the second array having a second wavelength between 400 and 700 nanometers, the second wavelength distinct from the first wavelength;

a third array of LEDs interleaved with the first and second arrays, each LED of the third array having a third wavelength between 800 and 2500 nanometers; and a fourth array of LEDs interleaved with the first, second, and third arrays, each LED of the fourth array emitting broadband light, wherein the LEDs of each of the respective arrays are spaced such that when each of the respective arrays is activated individually, the uniform illumination source uniformly illuminates the camera calibration target.

For some applications, the total number of LEDs is between 16 and 100.

The present invention will be more fully understood from the following detailed description of applications thereof, taken together with the drawings, in which:

DETAILED DESCRIPTION

Figure 1:
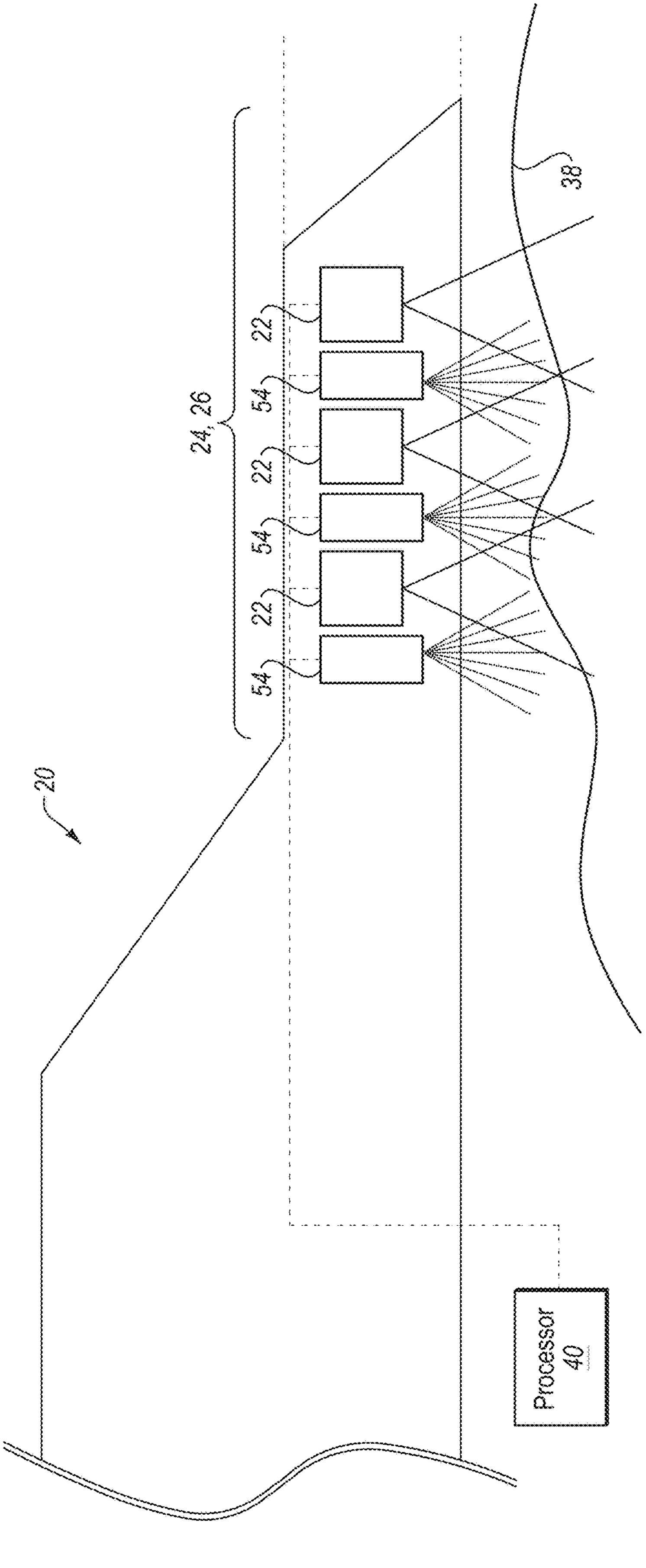
FIG. 1 is a schematic illustration of an elongate handheld wand for intraoral scanning, in accordance with some applications of the present invention.

Reference is now made to FIG. 1, which is a schematic illustration of an elongate handheld wand 20 for intraoral scanning, in accordance with some applications of the present invention. For some applications, elongate handheld wand 20 has a probe 24 at distal end 26 of handheld wand 20. Elongate handheld wand 20 is typically used to obtain scanning data of an intraoral surface 38. One or more cameras 22 are disposed within probe 24, e.g., rigidly fixed within probe 24, and arranged within probe 24 such that cameras 22 receive rays of light from an intraoral cavity in a non-central manner, i.e., the relationship between points in 3D world-coordinate space and corresponding points on the camera sensors of the one or more cameras is described by a set of camera rays for which there is no single point in space through which all of the camera rays pass.

Figure 2:
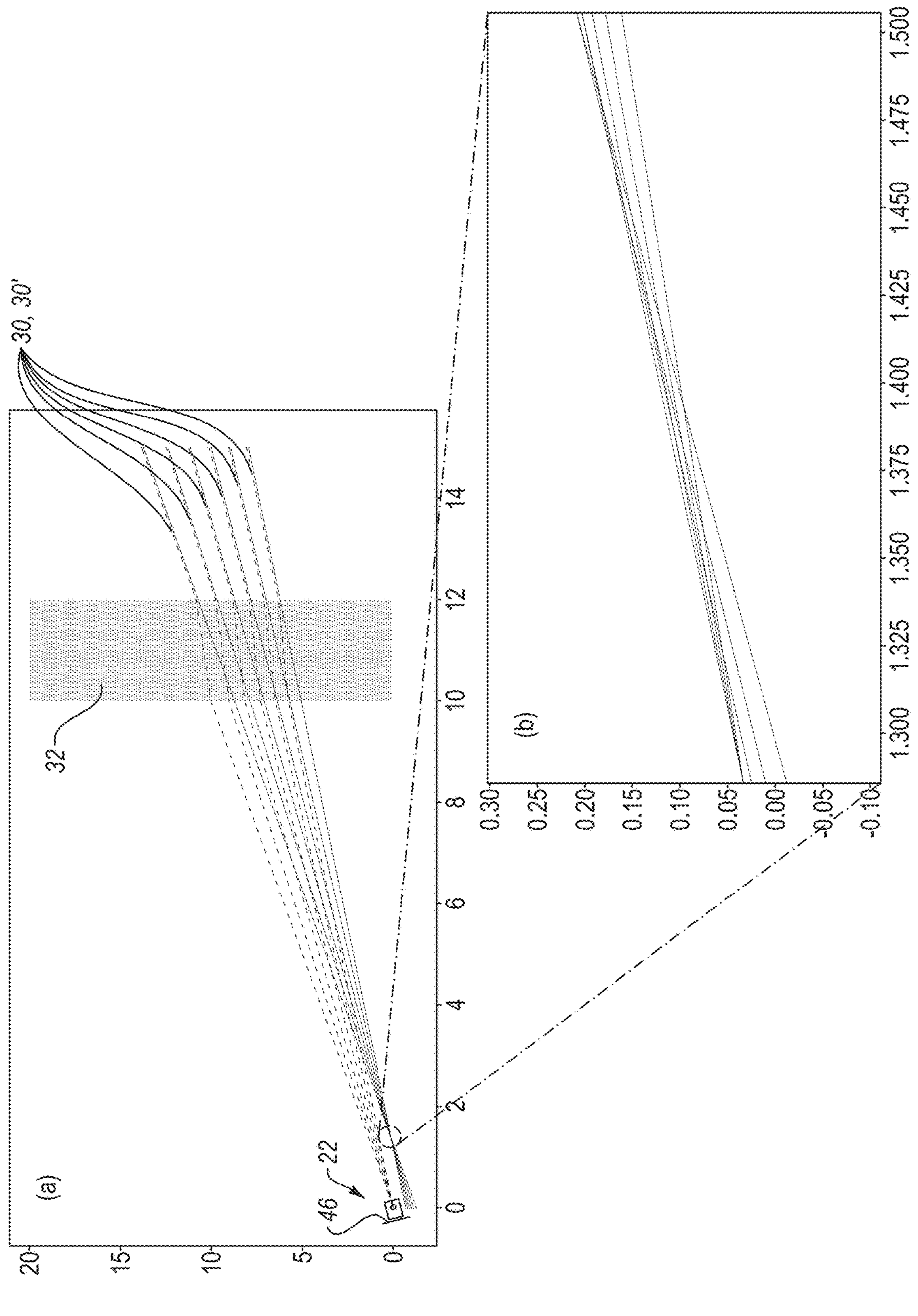
FIG. 2 is a schematic illustration of the non-central manner in which camera(s) of the elongate handheld wand receive rays of light, in accordance with some applications of the present invention.

Reference is now made to FIG. 2, which is a schematic illustration of the non-central manner in which cameras 22 receive rays of light, in accordance with some applications of the present invention. Each point (u,v) on a sensor of a camera 22 corresponds to a camera ray 30 in 3D world-coordinate space outside of elongate handheld wand 20. Light entering probe 24 along each one of these camera rays 30 reaches sensor 46 at a respective corresponding point (u,v) subsequently to refracting upon entering and then exiting a transparent window 32 of probe 24. Outside of probe 24, in 3D world-coordinate space, each camera ray 30 is associated with a vector 30' having a distinct origin and direction.

In order to geometrically calibrate each camera 22, these applications of the present invention use a relationship between points in 3D world-coordinate space and corresponding points (u,v) on the camera sensors. Thus, the correspondence between (i) a given vector 30' in 3D world-coordinate space along which light from a particular point in 3D world-coordinate space enters probe 24, and (ii) a specific point (u,v) on the sensor, is defined by the relationship. Part (a) of FIG. 2 appears to show a common point inside a dashed circle at which camera ray vectors 30' intersect. However, part (b) shows a zoomed-in view of the dashed circle, in which it can be seen that, in fact, there is no single point at which all of camera ray vectors 30' intersect.

Generally speaking, for a camera which operates in a central manner, camera rays in 3D world-coordinate space corresponding to each pixel on the camera sensor can be found by projecting rays from every pixel through a virtual pin-hole representing a point in which all of the camera rays intersect. It is noted that cameras 22 may be modeled as central cameras, however, factors of the overall optical system of handheld wand 20 cause cameras 22 to act in a non-central manner (further described hereinbelow with reference to FIG. 4), such that, as illustrated in FIG. 2, camera ray vectors 30' corresponding to light rays entering probe 24 do not intersect at a common point. Therefore, the standard camera pin-hole model does not provide an accurate enough definition for each camera ray vector 30'. As such, the non-central manner in which one or more cameras 22 receive the rays of light from the intraoral cavity introduces an image distortion. A computer processor 40 (shown in FIG. 1) generates a three-dimensional model of intraoral surface 38 based on images from one or more cameras 22. In order to obtain a desired level of accuracy in the three-dimensional model, computer processor 40 compensates for the image distortion specifically introduced by the non-central manner in which one or more cameras 22 receive the rays of light from the intraoral cavity, as further described hereinbelow with reference to FIG. 3.

For some applications, handheld wand 20 performs the intraoral scanning using structured light illumination. One or more structured light projectors 54 are disposed within handheld wand 20 and project a pattern of structured light, e.g., a pattern of spots, onto intraoral surface 38. In order for computer processor 40 to generate a three-dimensional model of intraoral surface 38 based on images from one or more cameras 22, computer processor 40 solves a "correspondence problem," where a correspondence between pattern elements in the structured light pattern and pattern elements seen by a camera 22 viewing the pattern is determined. For some applications, computer processor 40 compensates for the image distortion specifically introduced by the non-central manner in which one or more cameras 22 receive rays of light from the intraoral cavity by altering the coordinates of one or more of the structured light pattern elements as seen by one or more cameras 22 in order to account for the non-central manner in which the one or more cameras 22 receive rays of light from the intraoral cavity.

Figure 3:
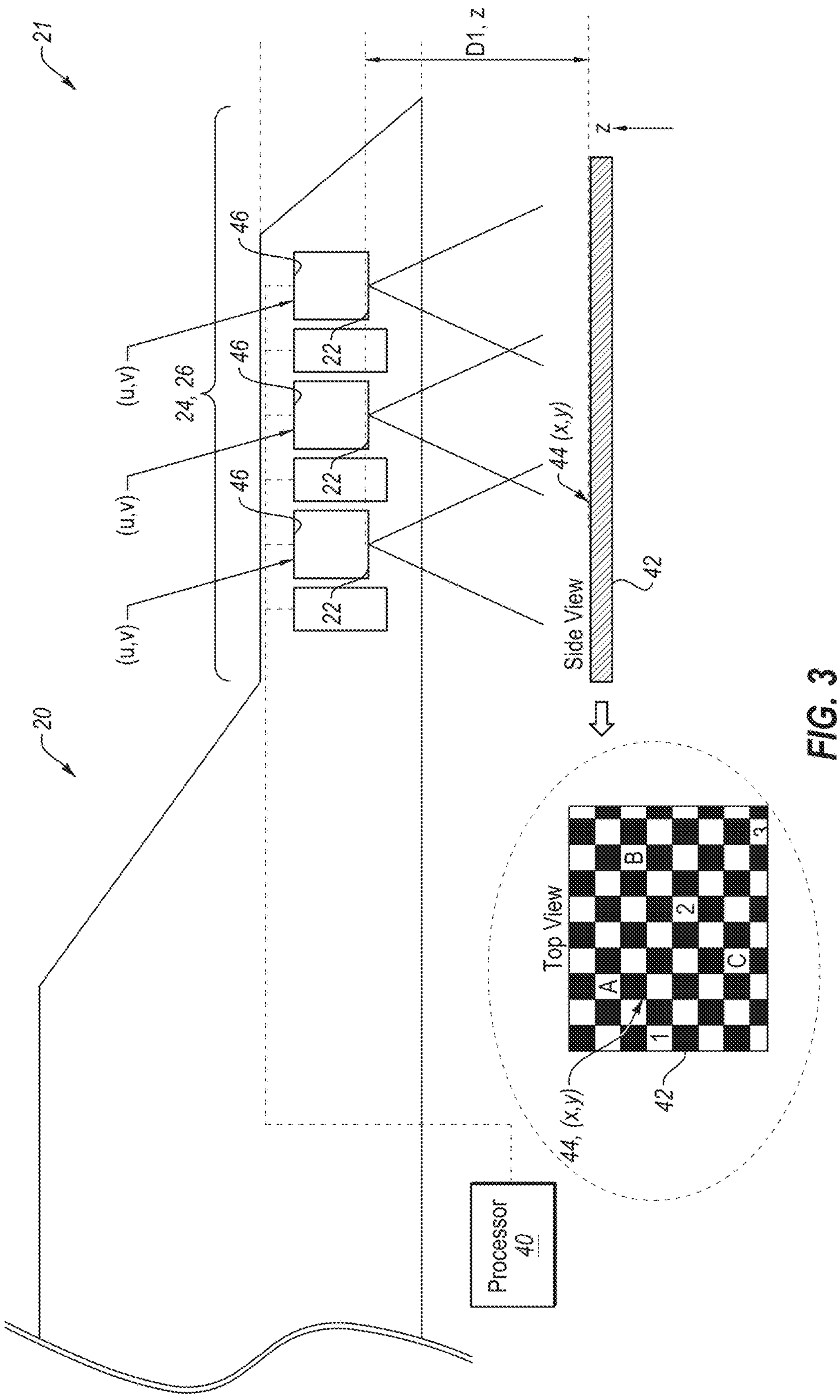
FIG. 3 is a schematic illustration of a camera calibration system for the elongate handheld wand, in accordance with some applications of the present invention.

Reference is now made to FIG. 3, which is a schematic illustration of a camera calibration system 21 for elongate handheld wand 20, in accordance with some applications of the present invention. In order to compensate for the image distortion specifically introduced by the non-central manner in which one or more cameras 22 receive the rays of light from the intraoral cavity, computer processor 40 analyzes the scanning data using camera calibration data that indicates a ray having a distinct origin and direction corresponding to each point (u,v) on sensor 46. The camera calibration data is generated by capturing, using one or more cameras 22, calibration images of a 2D camera calibration target 42 having a plurality of distinct calibration features 44, the capturing of the calibration images performed while 2D camera calibration target 42 is disposed at a respective plurality of distances D1, in a given direction z in space, from one or more cameras 22.

For example, 2D camera calibration target 42 may be a checkerboard target, e.g., a black and white checkerboard target, with the corner intersections of squares of different colors used as distinct calibration features 44. Alternatively or additionally, camera calibration target 42 has unique markings as well, such as letters and numbers, so that the relative positioning of the one or more cameras 22 may be determined. Each distinct calibration feature is given a corresponding coordinate value (x,y). Each respective distance D1 is given a value in the z-direction, with z=0 being at an arbitrary selected distance from one or more cameras 22. For example, z=0 may be selected as a distance very near transparent window 32 of probe 24 or sleeve-window 58 (as described hereinbelow with reference to FIG. 5A). Thus, when calibration images of 2D camera calibration target 42 are captured at a plurality of accurately controlled distances D1, each distinct calibration feature 44 has known (x,y,z) values. Processor 40 models a relationship between (i) points in 3D space defined by an (x,y,z) coordinate system and (ii) corresponding points (u,v) on sensor 46 of one or more cameras 22, as a set of camera rays using a model in which x,y as a function of u,v varies linearly with distance along z.

For each calibration image captured with camera calibration target 42, points (u,v) on sensor 46 which correspond to the distinct calibration features are known, and the (x,y,z) coordinates of the distinct calibration features in 3D world-coordinate space are known. Correspondence is solved such that each point (u,v) on sensor 46 which detects a distinct calibration feature corresponds to a known point in 3D world-coordinate space. Typically, a set of rays is then modeled as a function that takes a given (u,v,z) and outputs a corresponding (x,y), i.e., the function describes a linear transformation $R^3 \rightarrow R^2:(u,v,z) \rightarrow (x,y)$. The function is typically in the form of:

$$F(u, v, z) = G1(u, v) + z * G2(u, v) \quad \text{[Eqn. 1]}$$

which describes a camera ray in which G1(u,v) is a function that outputs an x,y corresponding to z=0 and G2(u,v) is a function that outputs an x,y corresponding to z=1. Thus, for each given (u,v,z) there is one and only one corresponding (x,y) coordinate.

For some applications, functions G1 and G2 can be defined as high order polynomial functions defined as:

$$G_i = \sum_k^N w_k^{(i)} \times g_k = \vec{w}^{(i)} \cdot \vec{g} \quad \text{[Eqn. 2]}$$

where $g_k \epsilon v^{\alpha} * u^{\beta}$ is a polynomial coefficient. The functions can be found using least-square minimization.

The terms can now be written as a linear equation:

$$F(u, v, z) = G_1(u, v) + z \times G_2(u, v) = \vec{w}^{(1)} \cdot \vec{g} + \vec{w}^{(2)} \cdot z \times \vec{g} = \vec{w}^{(*)} \cdot \vec{g}^{(*)} \quad \text{[Eqn. 3]}$$

The problem can then be separated to separately find a function of (u,v,z) that outputs (x) and a function of (u,v,z) that outputs (y). For stability, the input data is normalized to be within [−1,1]. It is noted that fitting $g_k$ can be done using polynomial fit, or any other type of function, e.g., radial basis function (RBF) fit.

Figure 4:
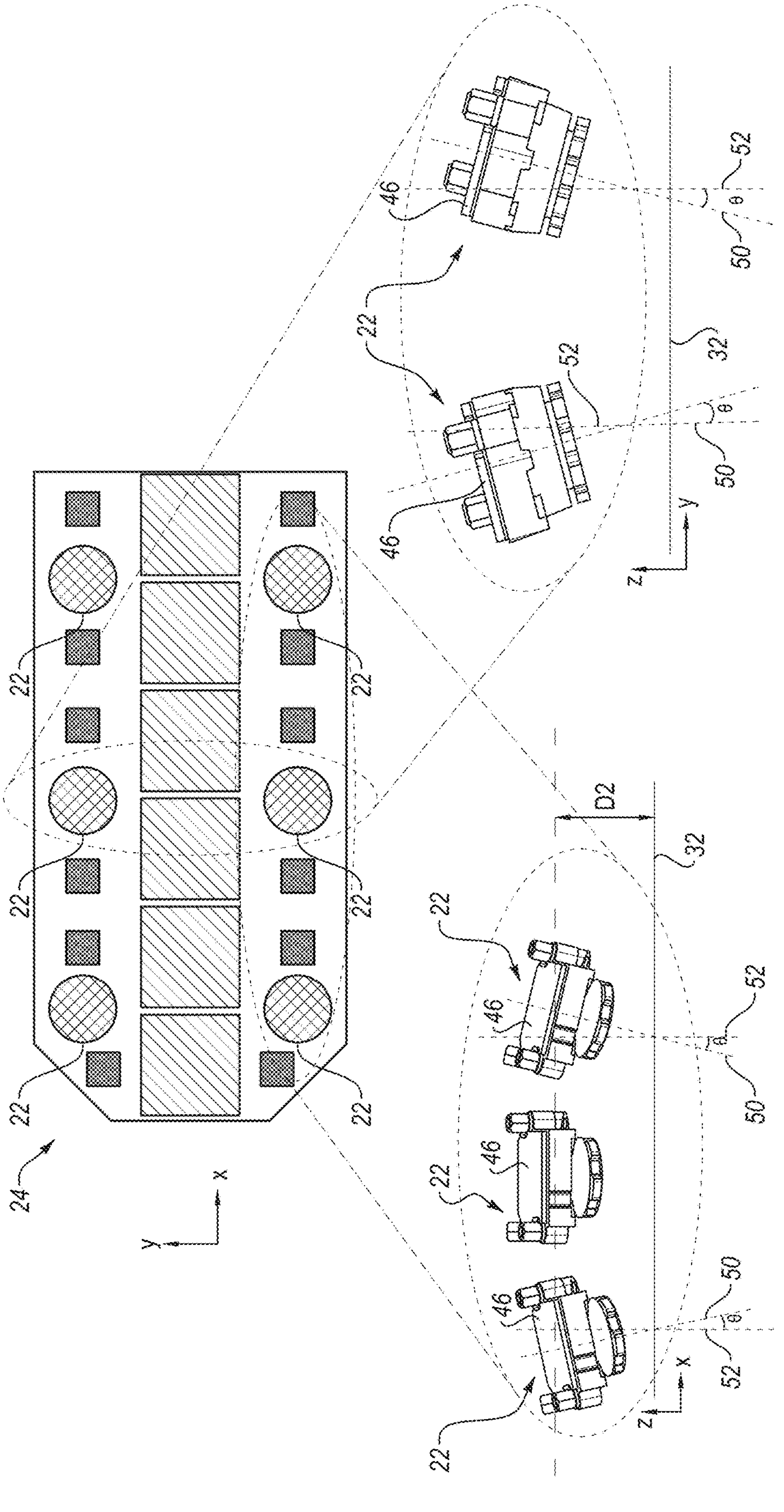
FIG. 4 is a schematic illustration of cameras disposed within a probe of the elongate handheld wand, in accordance with some applications of the present invention.

Reference is now made to FIG. 4, which is a schematic illustration of cameras 22 disposed within probe 24 of handheld wand 20, in accordance with some applications of the present invention. It is noted that, for some applications, cameras 22 are themselves central cameras, however, factors of the overall optical system of handheld wand 20 cause cameras 22 to act in the non-central manner described hereinabove. Alternatively, cameras 22 are non-central cameras. For applications in which cameras 22 are central cameras, one factor that contributes to the non-central manner in which cameras 22 receive rays of light from the intraoral cavity is the close proximity between cameras 22 and the intraoral surface 38 being scanned (see FIG. 1). This is due in part to an average distance D2 between camera sensors 46 of cameras 22 and a transparent window 32 of probe 24 typically being at least 50 mm and/or less than 200 mm. Another factor that contributes to the non-central manner in which cameras 22 receive rays of light from the intraoral cavity is that the rays of light pass through transparent window 32 of probe 24. In particular, cameras 22 are typically arranged such that their respective optical axes 50 are not perpendicular to transparent window 32 i.e., each optical axis 50 of a camera 22 forms an angle theta with respect to a normal axis 52 of transparent window 32 that is at least 7 degrees and/or less than 45 degrees.

Figure 5A:
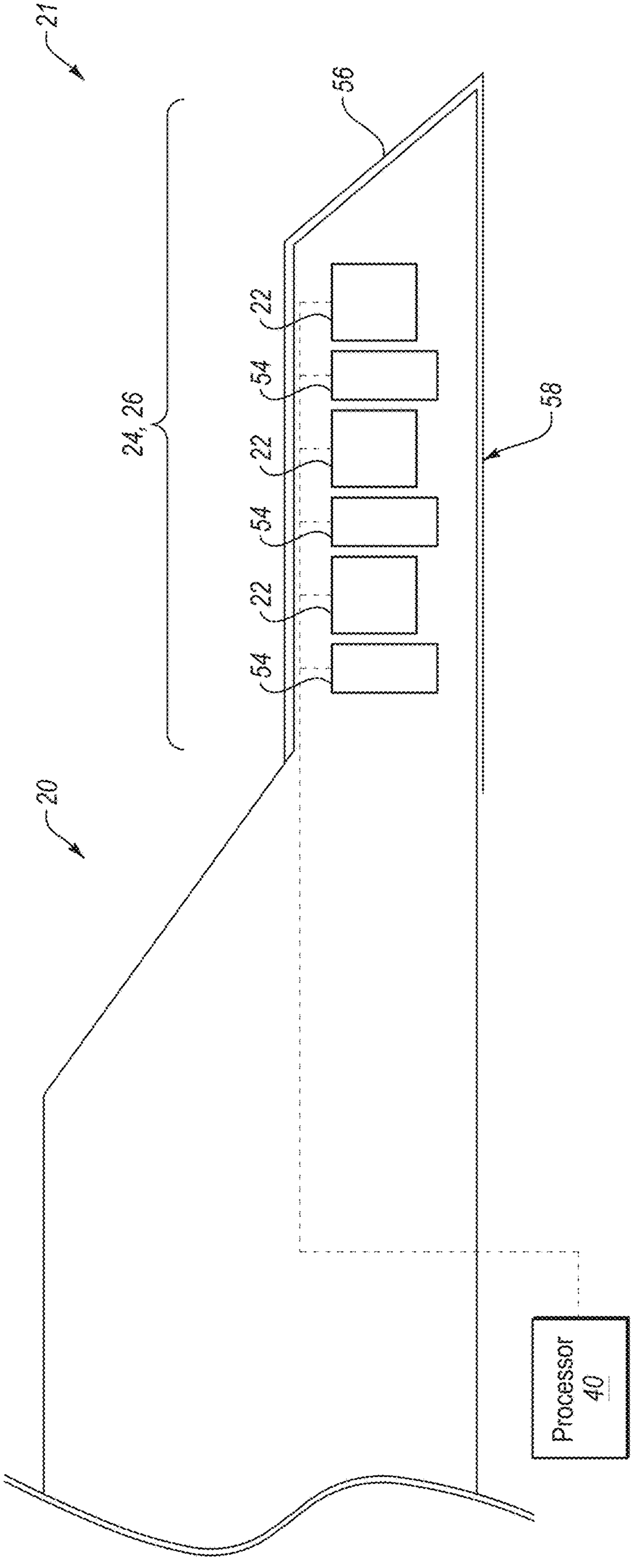
FIG. 5A is a schematic illustration of the elongate handheld wand with a sleeve positioned over the probe of the elongate handheld wand, in accordance with some applications of the present invention.

Reference is now made to FIG. 5A, which is a schematic illustration of elongate handheld wand 20 with a sleeve 56 positioned over probe 24 of elongate handheld wand 20, such that a sleeve-window 58 is positioned between intraoral surface 38 and transparent window 32 of probe 24, in accordance with some applications of the present invention.

For some applications, the entire sleeve 56 is transparent such that sleeve-window 58 refers to the specific area of transparent sleeve 56 which lines up with transparent window 32 of probe 24 when sleeve 56 is placed over probe 24. For some applications, sleeve 56 itself is not transparent, but rather has a transparent sleeve-window 58 that lines up with transparent window 32 (FIG. 4) of probe 24 when sleeve 56 is placed over probe 24. Typically, sleeve 56 is placed over probe 24 for hygienic reasons, e.g., a new sleeve is used for each patient. The addition of transparent sleeve-window 58 of sleeve 56 through which light rays exit and enter probe 24 during scanning typically changes the overall optical conditions of the intraoral scanner. Thus, in order to achieve high-accuracy 3D digital reconstruction of scanned intraoral surface 38, the changes in the optical conditions due to the presence of a sleeve are accounted for during a calibration process of the intraoral scanner, further described hereinbelow.

Figure 5B:
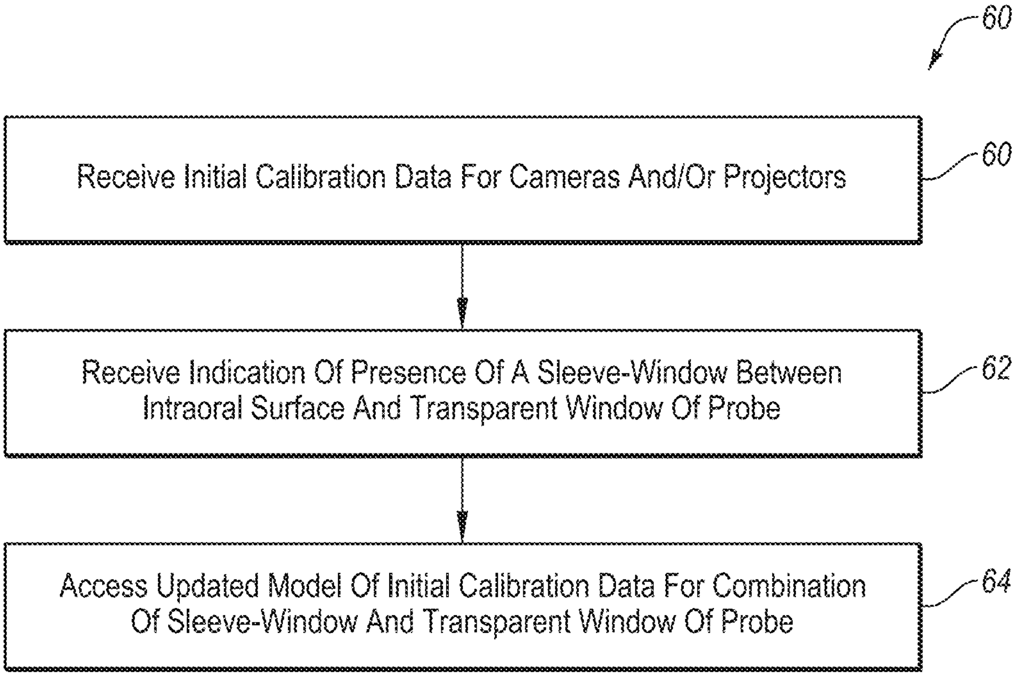
FIG. 5B is a flow chart depicting how changes in the optical conditions due to the presence of the sleeve are accounted for, in accordance with some applications of the present invention.

Reference is now made to FIG. 5B, which is a flow chart depicting how the changes in the optical conditions due to the presence of sleeve 56 are accounted for, in accordance with some applications of the present invention. As described hereinabove, elongate handheld wand 20 is used to obtain scanning data of intraoral surface 38. Elongate handheld wand includes probe 24 at distal end 26 of handheld wand 20, one or more cameras 22 disposed within probe 24 and arranged to receive light from intraoral surface 38 through transparent window 32 of probe 24, and one or more structured light projectors 54 arranged to project structured light onto intraoral surface 38 through transparent window 32 of probe 24. In step 60, computer processor 40 receives initial calibration data for the one or more cameras 22 and/or the one or more structured light projectors 54. As further described hereinbelow, for each camera 22 and each structured light projector 54, the initial calibration data includes a respective set of rays.

The initial calibration data for the one or more cameras 22 models the relationship between points in 3D space (x,y,z) and corresponding points (u,v) on sensors 46 of the one or more cameras 22 as a set of camera rays, each camera ray having an origin $O_i$ and a direction, as follows:

For each camera 22, the points (u,v) on sensor 46 form a grid of points.

For each point on the (u,v) grid of sensor 46, Eqn. 1 is used to find two (x,y, z) points, Pt1 and Pt2, in 3D world-coordinate space, each at a distinct z-value.

A camera ray $R_i$ is formed for each point on the (u,v) grid of sensor 46 by setting the origin of camera ray $R_i$ to be at Pt1 and defining the direction of camera ray $R_i$ as Pt2 minus Pt1 (Pt2−Pt1).

Thus, the initial calibration data for each camera 22 includes a camera ray $R_i$ corresponding to each point (u,v) on camera sensor 46, each camera ray $R_i$ having an origin $O_i$ and a direction.

Figure 6:
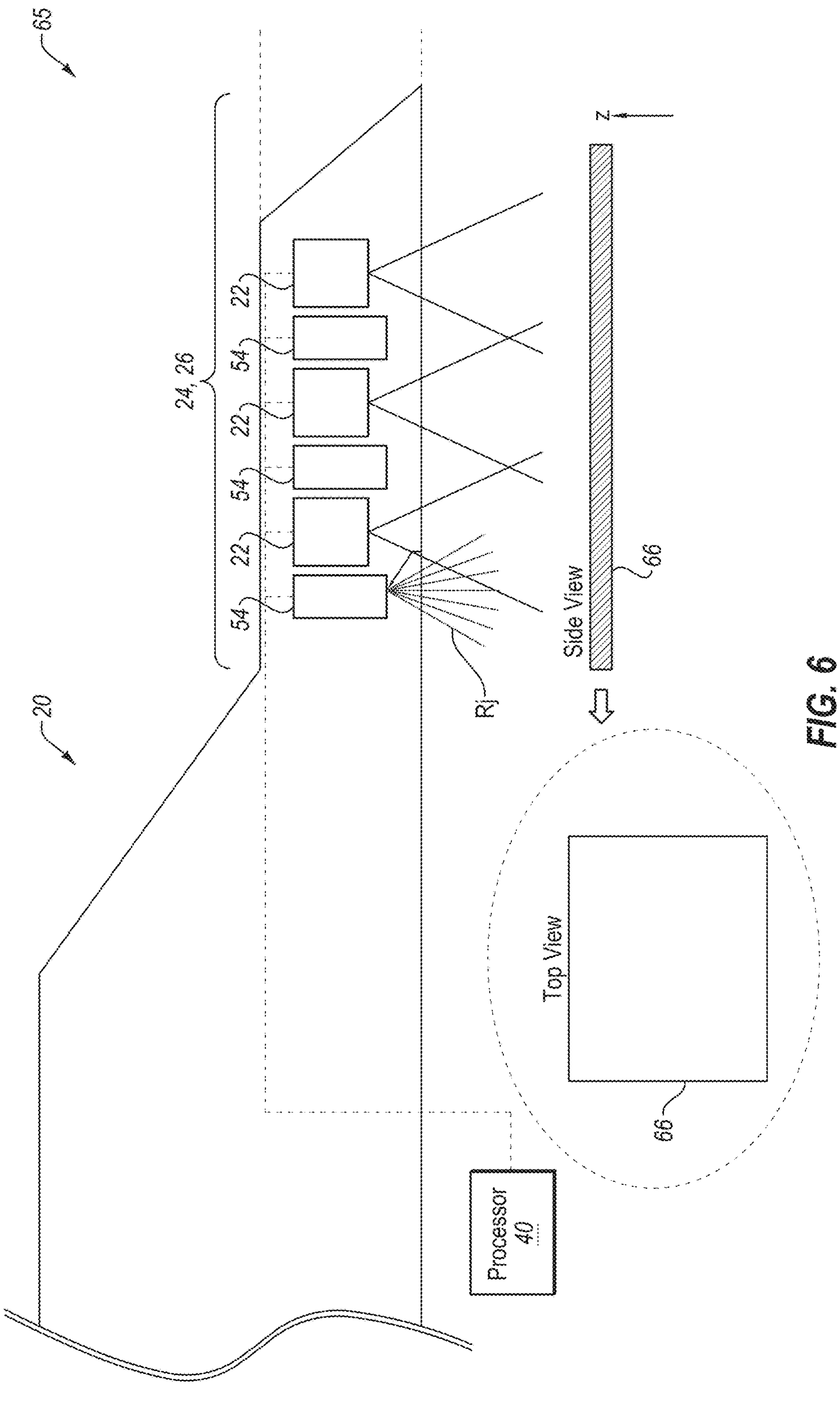
FIG. 6 is a schematic illustration of a projector calibration system for the elongate handheld wand, in accordance with some applications of the present invention.

For the one or more structured light projectors 54, each structured light projector 54 projects a plurality of structured light features, each projected structured light feature corresponding to a distinct projector ray $R_j$. The initial calibration data for one or more structured light projectors 54 defines an origin $O_j$ and a direction vector for each projector ray $R_j$, as follows:

Each structured light projector 54 is activated to project a pattern onto a 2D diffusive calibration target 66 (shown in FIG. 6).

Using one or more cameras 22, projector calibration images are captured while 2D diffusive calibration target 66 is disposed at a plurality of distinct z-values.

Based on the projector calibration images, (u,v) coordinates on camera sensors 46 are found for each detected pattern feature (e.g., spot) $S_j$ at each z-value of 2D diffusive calibration target 66.

Using the initial calibration data for the one or more cameras 22, for each detected pattern feature $S_j$ captured while 2D diffusive calibration target 66 is disposed at a given z-value, an (x,y,z) point can be found in 3D world-coordinate space at the intersection of (i) the camera ray $R_i$ corresponding to the (u,v) coordinate of the detected pattern feature $S_j$, and (ii) a z-plane at the z-value of 2D diffusive calibration target 66.

Such (x,y,z) points are found for each detected pattern feature $S_j$ at a plurality of different z-values.

A correspondence algorithm is then solved in order to determine which of the (x,y,z) points in 3D world-coordinate space corresponds to each projector ray $R_j$.

For each projector ray $R_j$, a line is then fitted to the (x,y,z) points corresponding to that projector ray $R_i$ in order to obtain an origin $O_j$ and direction vector for each projector ray $R_j$.

In step 62, computer processor 40 receives an indication of the presence of sleeve-window 58 positioned between intraoral surface 38 and transparent window 32 of probe 24. The optical properties of sleeve-window 58, e.g., a thickness of sleeve-window 58 and the index of refraction of sleeve-window 58 are typically known. Thus, the effect of the optical properties of sleeve-window 58 on light rays passing through sleeve-window 58 can be mathematically modeled. Each ray of light passing through sleeve-window 58 is shifted such that the origin of the light ray is altered while the propagation direction of the light ray remains unchanged. Thus, for a sleeve-window of given optical properties, (a) an updated model of the initial calibration data for one or more cameras 22 is calculated by mathematically shifting origin $O_i$ for each camera ray $R_i$, and (b) an updated model of the initial calibration data for one or more structured light projectors 54 is calculated by mathematically shifting origin Oj for each projector ray $R_j$. For some applications, updated sets of camera rays and projector rays may be stored for a plurality of different sleeve-windows having different respective optical properties. Thus, in step 64, in response to the indication that sleeve-window 58 is positioned between intraoral surface 38 and transparent window 32 of probe 24, i.e., in response to an indication that sleeve 56 has been placed over probe 24, computer processor 40 accesses an updated model of the initial calibration data for the combination of transparent window 32 of probe 24 and sleeve-window 58, the updated model calculated from the initial calibration data based on an optical property of sleeve-window 58.

Updating the initial calibration data mathematically to account for the presence of sleeve-window 58 allows handheld wand 20 to be used for intraoral scanning with a variety of different types of sleeves, i.e., sleeves having a variety of different optical properties, without having to redo the initial calibration process of cameras 22 and/or structured light projectors 54. Updating the initial calibration data mathematically to account for the presence of sleeve-window 58 also allows the initial calibration process to be performed without having to add a physical window to the calibration jig in order to simulate the presence of sleeve-window 58. Thus, the calibration jig is simpler and can be kept more stable.

Reference is now made to FIG. 6, which is a schematic illustration of a projector calibration system 65 for elongate handheld wand 20, in accordance with some applications of the present invention. As described hereinabove, initial calibration of one or more structured light projectors 54 is performed by activating each structured light projector 54 in turn to project a plurality of structured light features, e.g., spots, onto 2D diffusive calibration target 66 and capturing projector calibration images using one or more cameras 22 of the structured light features projected onto 2D diffusive calibration target 66, while 2D projector calibration target is disposed at a plurality of different z-values. Each projected structured light feature corresponds to a distinct projector ray $R_j$. Structured light projectors 54 are typically laser projectors and as such there may be speckle noise in the projector calibration images. For some applications, in addition to moving 2D diffusive calibration target 66 in the z-direction, 2D diffusive calibration target 66 is also moved in the (x,y) plane in order to reduce the speckle noise.

Figure 7:
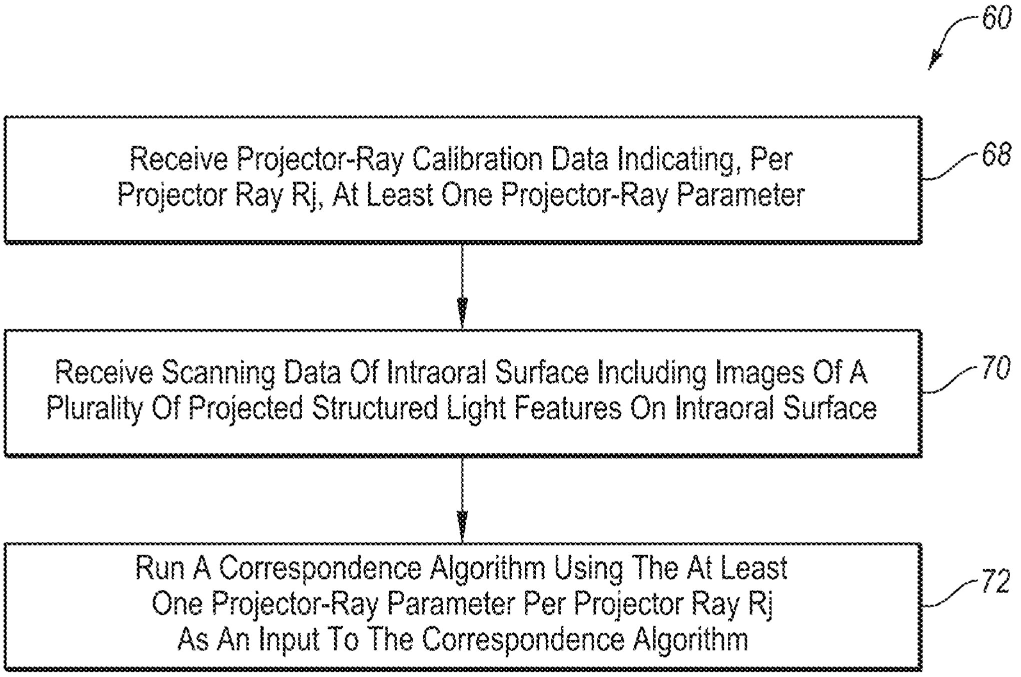
FIG. 7 is a flow chart depicting a method for learning projector-ray parameters during calibration and subsequently utilizing the learned projector-ray parameters to help solve a correspondence algorithm during intraoral scanning, in accordance with some applications of the present invention.

Reference is now made to FIG. 7, which is a flow chart depicting a method for learning projector-ray parameters of each projector ray $R_j$ during calibration and subsequently utilizing the learned projector-ray parameters to help solve the correspondence algorithm during intraoral scanning, in accordance with some applications of the present invention. In addition to learning the position (origin and direction) of each projector ray $R_j$, during the initial projector calibration process, other parameters of each projector ray $R_j$ for each structured light projector 54 are learned by computer processor 40. These additional parameters may be used to help differentiate and identify structured light features projected on intraoral surface 38 when the correspondence algorithm is solved during an intraoral scan. For some applications, the projected structured light features are created by activating a laser of structured light projector 54 to project light through a diffractive optical element (DOE). The learned parameters of each projector ray $R_j$ are a function of the design of the DOE.

In step 68, computer processor 40 receives projector-ray calibration data indicating, for each projector ray $R_j$, at least one projector-ray parameter. For some applications, the projector-ray parameter for each projector ray $R_j$ may be a shape of the projected structured light feature corresponding to projector ray $R_j$ based on (1) a plurality of calibration images of the projected structured light feature on a calibration target, e.g., 2D diffusive calibration target 66, and (2) a known respective angle at which projector ray $R_j$ was incident on the calibration target for each calibration image. For example, the shape of structured light feature $S_j$ may be an ellipsoid which changes in response to the angle at which projector ray $R_j$ is incident on the calibration target. Additionally or alternatively, the projector-ray parameter for each projector ray $R_j$ may be an intensity of projector ray $R_j$ based on a plurality of calibration images of the projected structured light feature on a calibration target, e.g., 2D diffusive calibration target 66. Furthermore, the projector-ray parameter(s) typically change smoothly with depth. For some applications, the projector-ray calibration data received by computer processor 40 includes how each projector-ray parameter changes with depth.

In step 70, computer processor 40 receives scanning data of intraoral surface 38, the scanning data comprising images of a plurality of projected structured light features on intraoral surface 38. In step 72, computer processor 40 runs a correspondence algorithm to identify which projected structured light feature on intraoral surface 38 corresponds to each respective projector ray $R_j$, using the at least one project-ray parameter per projector ray $R_j$ as an input to the correspondence algorithm. For example, the projector-ray parameter(s) for each projector ray $R_j$ may help the correspondence algorithm identify which projected structured light features match which respective projector rays $R_j$. Additionally or alternatively, the projector-ray parameter(s) for each projector ray Rj may help the correspondence algorithm differentiate between image features that are true projected structured light features and image features that are false alarms.

Figure 8:
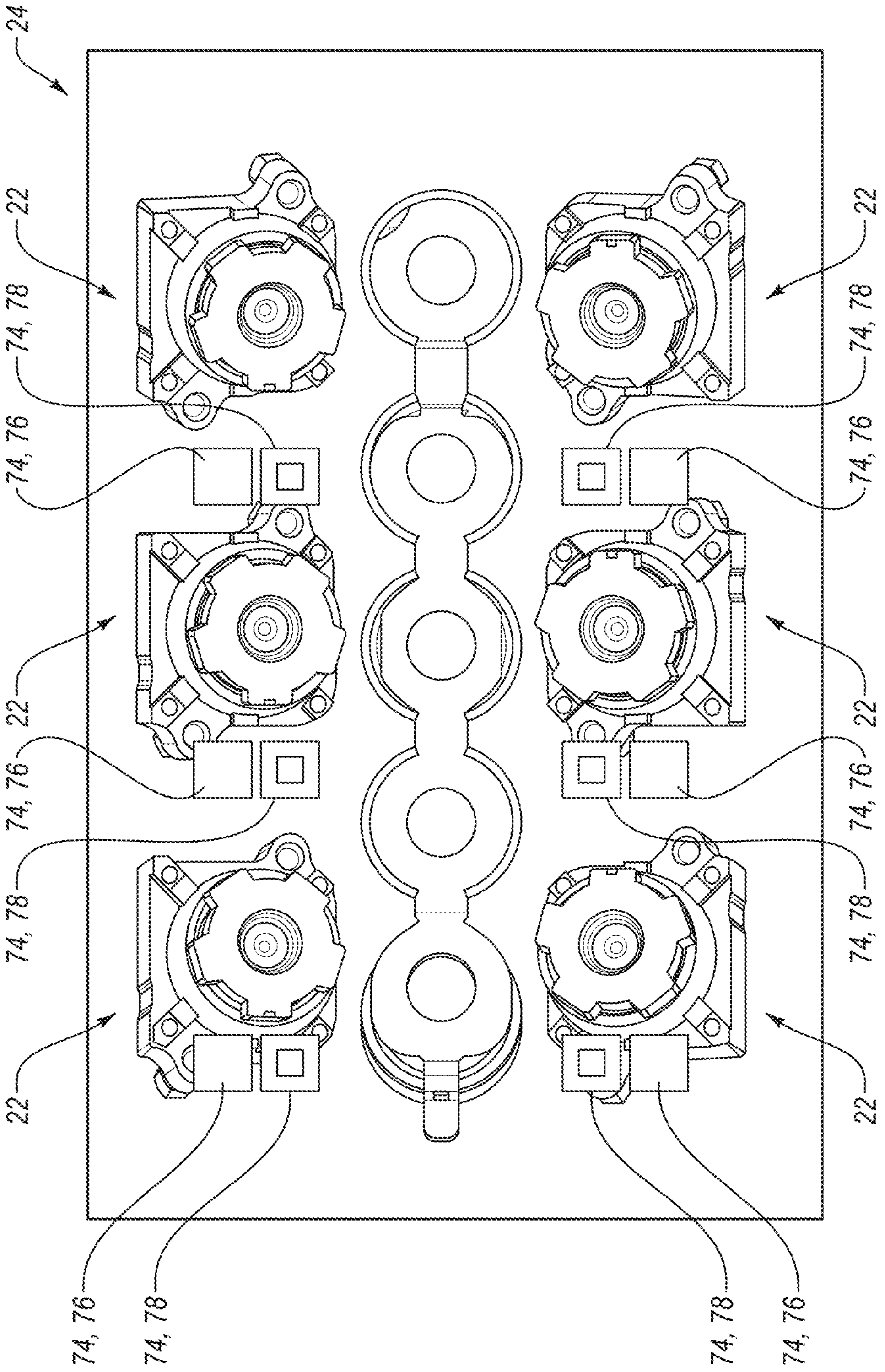
FIG. 8 is a schematic illustration of the probe, in accordance with some applications of the present invention.

Reference is now made to FIG. 8, which is a schematic illustration of probe 24, in accordance with some applications of the present invention. For some applications, images of intraoral surface 38 are captured under non-structured light, e.g., broad spectrum light and/or Near Infra-Red (NIR). Typically, one or more non-structured illumination sources 74 are disposed within handheld wand 20, and arranged such that images of intraoral surface 38 are captured using one or more cameras 22 under non-uniform illumination from one or more non-structured illumination sources 74. The non-uniformity of the illumination is generally due to the close proximity of scanned intraoral surface 38 to probe 24. For some applications, non-structured illumination sources 74 are disposed within probe 24, as shown in FIG. 8. Alternatively or additionally, non-structured light sources 74 may be disposed within a handle of handheld wand 20, and the light from non-structured illumination sources 74 may be led to probe 24 via a light pipe or optical fiber (configuration not shown). Non-structured illumination sources 74 may be broad spectrum illumination sources 76, e.g., white light LEDs, and/or NIR illumination sources 78. Due to the close proximity of the scanned intraoral surface 38 to probe 24, the illumination from one or more non-structured light sources 74 is incident on intraoral surface 38 in a non-uniform manner, i.e., images of intraoral surface 38 are captured using one or more cameras 22 under non-uniform illumination from one or more non-structured illumination sources 74.

Figure 9A:
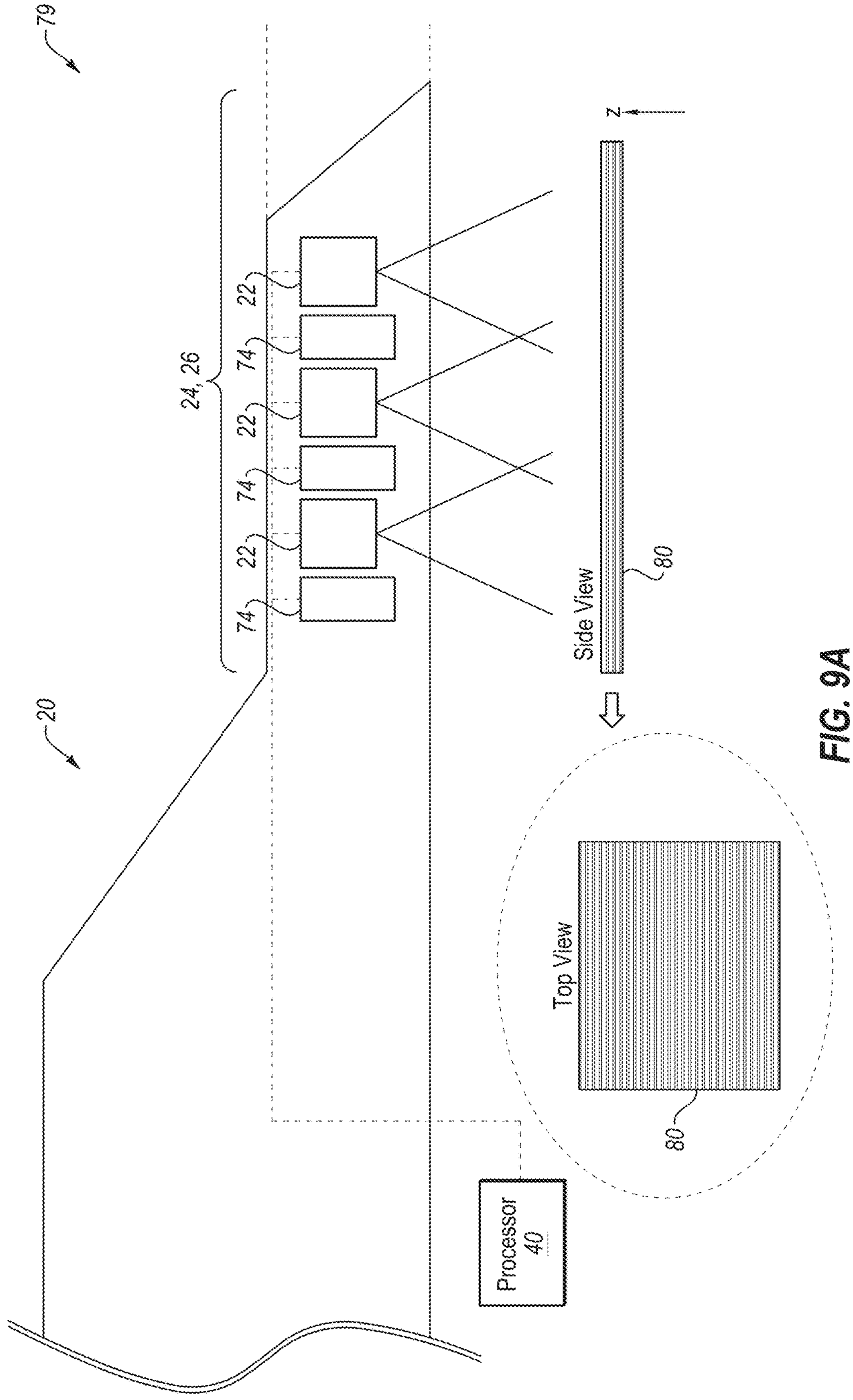
FIGS. 9A-B show a calibration system and an example calibration image, respectively, used to compensate for non-uniformity of the illumination from non-structured illumination sources of the elongate handheld wand, in accordance with some applications of the present invention.
Figure 9B:
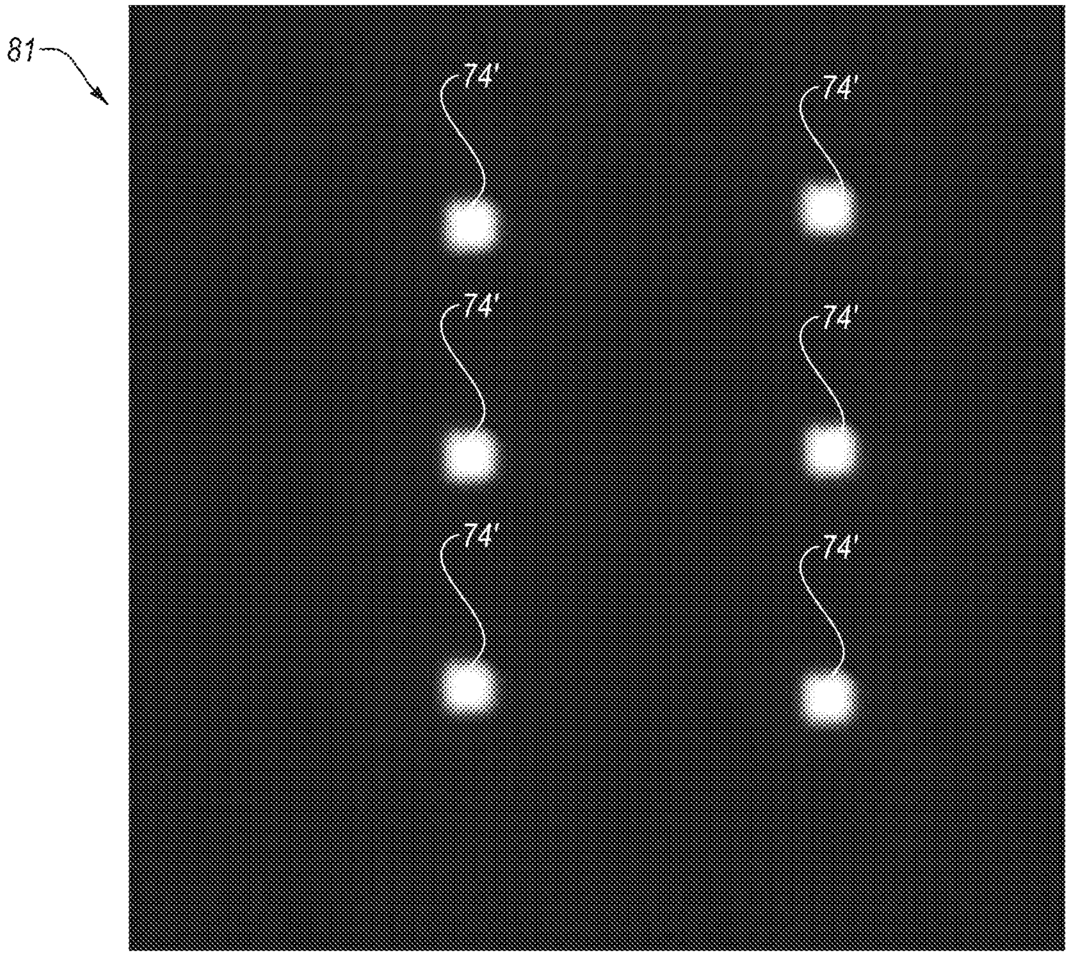

Reference is now made to FIGS. 9A-B, which show a calibration system 79 and an example calibration image 81, respectively, used to compensate for the non-uniformity of the illumination from non-structured illumination sources 74, in accordance with some applications of the present invention. For some applications, in order to compensate for the non-uniformity of the illumination, for each manufactured intraoral scanner, i.e., for each manufactured handheld wand 20, a mathematical model of the illumination from the specific one or more non-structured illumination sources 74 of that specific handheld wand 20 is calculated and stored as part of the initial calibration data for that specific intraoral scanner. Computer processor 40 analyzes the images captured by one or more cameras 22 under the non-uniform illumination from one or more non-structured illumination sources 74 of a given handheld wand 20 and compensates for the non-uniformity of the illumination using the calibration data that includes the mathematical model of the illumination from the specific one or more non-structured illumination sources 74 of that given handheld wand 20. For some applications, the mathematical model of the illumination includes the location of each of one or more non-structured illumination sources 74 as seen in a 3D world-coordinate space by one or more cameras 22. One or more non-structured illumination sources 74 are activated to emit light onto a reflective calibration target 80, which acts as a mirror such that the calibration images taken of reflective calibration target 80 show a reflection 74' of each of the activated non-structured illumination sources 74 as seen by the camera 22 which captured the calibration image. Calibration images of reflective calibration target 80 are captured while reflective calibration target 80 is positioned at multiple different z-values. The specific points (u,v) on sensor 46 of each camera corresponding to the center of each reflection 74' taken at each z-value of reflective calibration target 80 are used to calculate the mathematical model of the illumination. Since reflective calibration target 80 acts as a mirror, non-structured light sources 74 as seen by cameras 22 appear to be positioned at a distance from reflective calibration target 80 that is larger than the actual distance between non-structured light sources 74 and reflective calibration target 80; this is accounted for in the calculation of the mathematical model of the illumination.

Thus, the mathematical model of the illumination from the specific one or more non-structured illumination sources 74 of each specific handheld wand 20 includes the location of each of one or more non-structured illumination sources 74 as optically seen in 3D world-coordinate space by one or more cameras 22 via images of reflective calibration target 80. It is noted that the mathematical model of the non-uniform illumination includes the location of each non-structured illumination source 74 as optically seen by one or more cameras 22, and not the actual physical location at which each non-structured illumination source 74 is disposed within handheld wand 20. For example, if non-structured illumination source(s) 74 are disposed within a handle of handheld wand 20 and light from non-structured illumination source(s) 74 is led to probe 24 by a light pipe or optical fiber, then the mathematical model of the non-uniform illumination includes the location of the tip of each light pipe or optical fiber that emits light out of probe 24, as optically seen by one or more cameras 22 via reflective calibration target 80.

For some applications, the size and/or shape of each non-structured illumination source 74, as seen by one or more cameras 22 via reflective calibration target 80, is stored as part of the calibration data. During a scan of a patient's intraoral surface 38, parts of intraoral surface 38 may be reflective and as such one or more cameras 22 may see a reflected non-uniform illumination source 74 in addition to projected pattern features. Having the size and/or shape of each non-uniform illumination source 74 as seen by the cameras stored in the calibration data may help computer processor 40 remove the reflection of non-uniform illumination source 74 from the correspondence algorithm.

For some applications, the calibration images of reflective calibration target 80 are acquired prior to the handheld wand 20 being packaged for commercial sale, i.e., as part of a manufacturing process of handheld wand 20. The mathematical model of the non-uniform illumination may also be updated once handheld wand 20 is already in commercial use based on captured scans of patients using that handheld wand. Thus, for some applications, computer processor 40 updates the mathematical model of the illumination from the specific one or more non-structured light sources 74 of a given handheld wand 20 after a given use of handheld wand 20 to scan an intraoral surface 38 of a patient and before a subsequent use of handheld wand 20 to scan an intraoral surface 38 of a patient.

For some applications, the mathematical model of the non-uniform illumination from the specific one or more non-structured illumination sources 74 of a given handheld wand 20 further includes camera-vignette calibration data indicative of a measure of relative illumination (e.g., vignetting) for each of the one or more cameras 22, and computer processor 40 further compensates for the non-uniformity of the illumination of one or more non-structured illumination sources 74 using the camera-vignette calibration data. The camera-vignette calibration data is generated by capturing, using one or more cameras 22, calibration images of 2D camera calibration target 42 (shown in FIG. 3) while 2D camera calibration target 42 is back-lit with uniform illumination. For each camera-vignette calibration image, an image of 2D camera calibration target 42 (which is a checkerboard target) is captured, and then 2D camera calibration target 42 is moved in the x-direction so that when a subsequent calibration image is captured, the dark, e.g., black, squares of 2D camera calibration target 42 are replaced by white squares. Computer processor 40 then merges the two camera-vignette calibration images to obtain an image showing only white squares. For some applications, the edges of the white squares may still be visible in the combined image; these can be removed by either adding more calibration images to the combined image or by image filtering. Once a uniform white image is obtained, computer processor 40 fits a relative illumination (e.g., vignetting) model for each camera 22.

Figure 10:
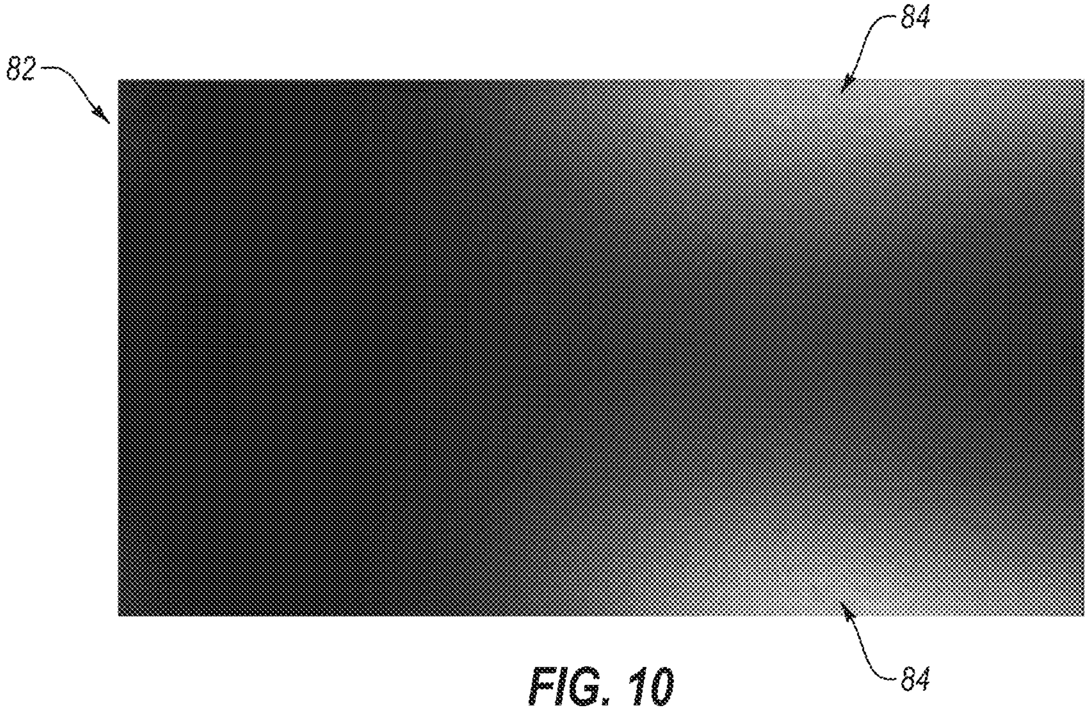
FIG. 10 shows an example calibration image used to compensate for the non-uniformity of the illumination from the non-structured illumination sources, in accordance with some applications of the present invention.

Reference is now made to FIG. 10, which shows an example calibration image 82 used to compensate for the non-uniformity of the illumination from non-structured illumination sources 74, in accordance with some applications of the present invention. Example calibration image 82 shows two respective areas 84 of illumination each from a respective non-structured illumination source 74, as captured by one camera 22. For some applications, the mathematical model of the non-uniform illumination from the specific one or more non-structured illumination sources 74 of a given handheld wand 20 includes an estimated illumination intensity-per-angle emitted from each non-structured illumination source 74, i.e., an intensity profile for each non-structured illumination source 74.

The estimated illumination intensity-per-angle emitted from each non-structured illumination source 74 is estimated based on calibration images captured using one or more cameras 22 of a 2D diffusive calibration target, such as 2D diffusive calibration target 66 shown in FIG. 6, illuminated with one or more non-structured illumination sources 74.

For some applications, the known positions of each non-structured illumination source 74 and camera-vignette calibration data are used when analyzing the calibration images used for estimating the intensity profile of each non-structured illumination source 74. Using known parameters of the specific non-structured illumination sources 74, e.g., known parameters of the LEDs, computer processor 40 simulates images of what 2D diffusive calibration target 66 would look like under non-uniform illumination from non-structured illumination sources 74. Actual calibration images of 2D diffusive calibration target 66 under non-uniform illumination from non-structured illumination sources 74 are captured using one or more cameras 22. Computer processor 40 then compares the simulated images to the actual images and uses a minimization process to update the parameters until the simulated images match the actual images, thus arriving at a parametric profile of the intensity and angular distribution of the illumination from the specific non-structured illumination sources 74 per given handheld wand 20.

For some applications, the mathematical model of the non-uniform illumination from the specific one or more non-structured illumination sources 74 of a given handheld wand 20 includes (i) the distance of a calibration target, e.g., reflective calibration target 80, or 2D diffusive calibration target 66, from transparent window 32 of probe 24 and (ii) Fresnel reflections from transparent window 32 of probe 24.

Alternatively or additionally, computer processor 40 analyzes images captured by one or more cameras 22 under the non-uniform illumination from one or more non-structured illumination sources 74 and compensates for the non-uniformity of the illumination using calibration data indicating an amount of light received at each point (u,v) on sensor 46 of one or more cameras 22 for different respective distances from the cameras. To generate the calibration data indicating an amount of light received at each point (u,v) on sensor 46, calibration images are captured, using the one or more cameras, of a 2D calibration target, e.g., a solid-color 2D calibration target, e.g., 2D diffusive calibration target 66. The capturing of the calibration images is performed while the 2D calibration target is disposed at a respective plurality of distances, in the z direction in space, from one or more cameras 22. Computer processor 40 fits a mathematical function to the calibration images corresponding to an amount of light received at each point (u,v) on sensor 46 of one or more cameras 22 for each of the respective plurality of distances in the z direction.

Figure 11:
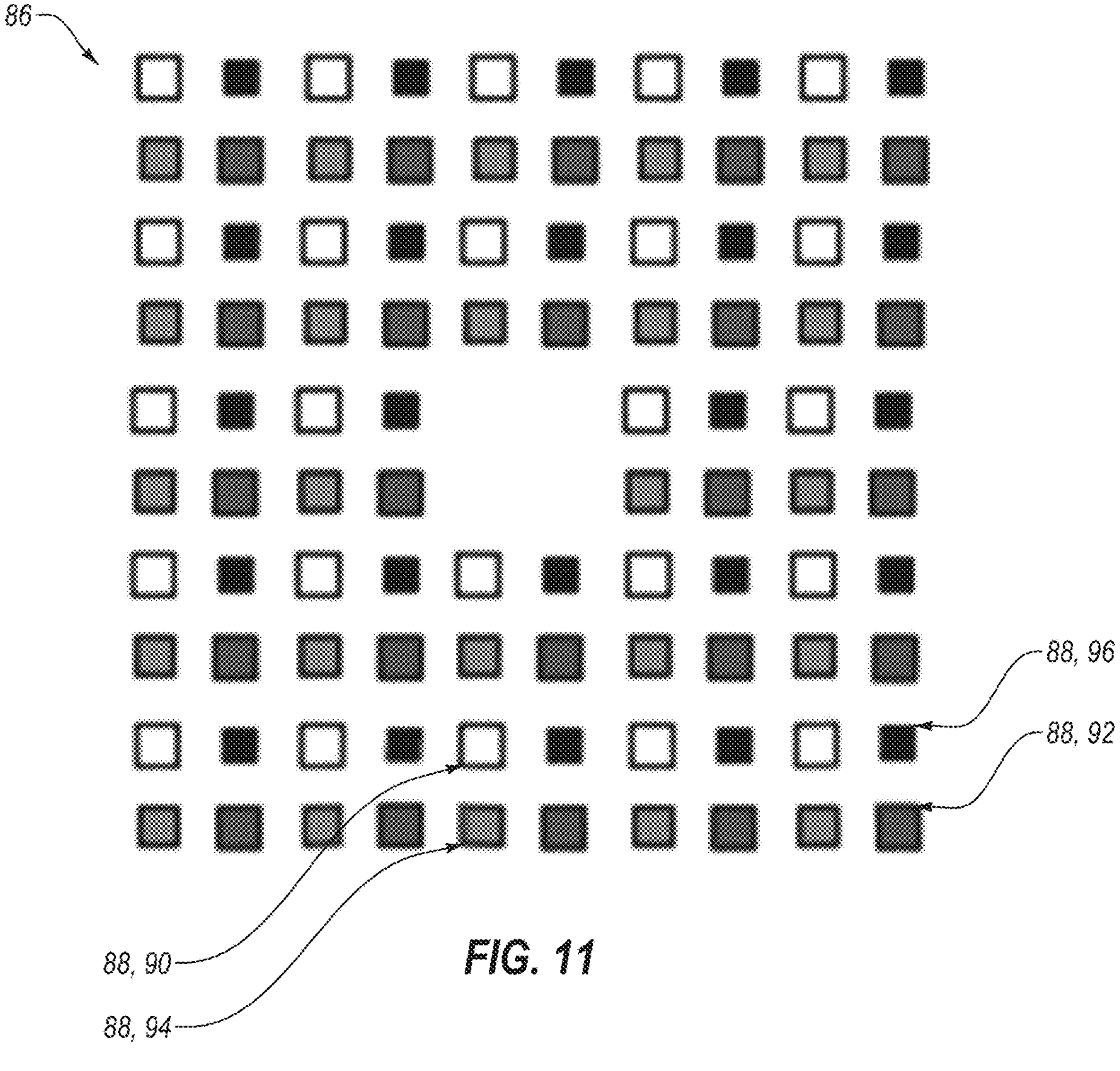
FIG. 11 is a schematic illustration of a uniform illumination source including multiple arrays of LEDs, each array having a different wavelength, in accordance with some applications of the present invention.

Reference is now made to FIG. 11, which is a schematic illustration of a uniform illumination source 86 made up of multiple arrays of LEDs, each array having a different wavelength, in accordance with some applications of the present invention. As described hereinabove, there are a plurality of different types of illumination sources utilized in handheld wand 20, e.g., structured light projectors 54 utilizing lasers in different colors, broad spectrum LEDs, and NIR illumination sources, e.g., NIR LEDs. In order to achieve high accuracy scanning, small deviations in the optics of one or more cameras 22 for different respective wavelengths, e.g., chromatic aberrations, are accounted for in the initial calibration process of one or more cameras 22. Thus, for some applications, the initial calibration of one or more cameras 22 of handheld wand 20 is repeated under illumination from each type of illumination that may be used during scanning. As described hereinabove, to calibrate one or more cameras 22, 2D camera calibration target 42 having a plurality of distinct calibration features is used, e.g., a checkerboard pattern optionally with additional unique markings such as letters and numbers. During calibration of one or more cameras 22, for each repetition of the calibration, 2D camera calibration target 42 is uniformly backlit with one of the various types of illumination that camera(s) 22 may encounter during intraoral scanning, such that the initial camera calibration data includes calibration data for each wavelength camera(s) 22 may encounter during intraoral scanning. For the broadband illumination, the calibration is repeated for each color-band of pixels on sensor(s) 46, e.g., for the red-band, blue-band, and green-band of the pixels on sensor(s) 46.

For some applications, in order to simplify the calibration system, a single uniform illumination source 86 includes multiple arrays of light emitting diodes (LEDs) 88, each array having one of the various different wavelengths. The LEDs 88 of each of the respective arrays are spaced such that when each of the respective arrays is activated individually, uniform illumination source 86 uniformly illuminates 2D camera calibration target 42.

For the broadband illumination and NIR illumination, uniform illumination source 86 includes a respective array of the same LEDs that are used in handheld wand 20. Structured light projector(s) 54 typically use blue and green laser light. In order to avoid speckle noise during the calibration process, green and blue LEDs having similar central wavelengths to the blue and green lasers of structured light projector(s) 54 are used in uniform illumination source 86. Thus, uniform illumination source 86 includes:

A first array of light emitting diodes (LEDs) 88, each specific LED 90 of the first array having a first wavelength between 400 and 700 nanometers, e.g., blue LEDs 90 having a similar central wavelength to a blue-laser structured light projector 54. For some applications, blue LEDs 90 of the first array are sized to be 2×2 mm.

A second array of LEDs 88 interleaved with the first array, each specific LED 92 of the second array having a second wavelength between 400 and 700 nanometers, the second wavelength distinct from the first wavelength, e.g., green LEDs 92 having a similar central wavelength to a green-laser structured light projector 54. For some applications, green LEDs 92 of the first array are sized to be 2×2 mm.

A third array of LEDs 88 interleaved with the first and second arrays, each specific LED 94 of the third array having a third wavelength between 800 and 2500 nanometers, i.e., NIR LEDs 94. For some applications, NIR LEDs 94 of the third array are sized to be 1.85×1.85 mm.

A fourth array of LEDs 88 interleaved with the first, second, and third arrays, each specific LED 96 of the fourth array emitting broadband light. For some applications, the broadband LEDs 96 of the fourth array are sized to be 1.5×1.5 mm.

For some applications, the total number of LEDs 88 in uniform illumination source 86 is between at least 16 and or less than 100. For some applications, the arrays of LEDs 88 in uniform illumination source are arranged such that the overall shape of uniform illumination source 86 is a square. The use of a square is such that uniform illumination source 86 matches the size and shape of 2D camera calibration target 42 which is uniformly backlit using uniform illumination source 86. If an alternative shape is used for 2D camera calibration target 42, then a corresponding alternative shape may be used for uniform illumination source 86.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 40. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 40) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 40) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Computer processor 40 is typically a hardware device programmed with computer program instructions to produce a special purpose computer. For example, when programmed to perform the methods described herein, the computer processor typically acts as a special purpose computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for intraoral scanning, the apparatus comprising:

an elongate wand comprising a probe at a distal end of the elongate wand;

one or more cameras disposed within the probe;

one or more non-structured illumination sources disposed within the elongate wand and arranged such that images of an intraoral surface are captured using the one or more cameras under non-uniform illumination from the one or more non-structured illumination sources; and a computer processor configured to analyze images captured by the one or more cameras under the non-uniform illumination from the one or more non-structured illumination sources, wherein the computer processor is configured to compensate for a non-uniformity of the non-uniform illumination using calibration data generated based on a mathematical model of the non-uniform illumination from the one or more non-structured illumination sources of the apparatus, the mathematical model including a location of each of the one or more non-structured illumination sources as seen in a 3D world-coordinate space by the one or more cameras via images of a reflective surface that acts as a mirror such that the images of the reflective surface show a reflection of each of the one or more non-structured illumination sources as seen by the one or more cameras.

2. The apparatus according to claim 1, wherein the computer processor is configured to update the mathematical model of the non-uniform illumination from the one or more non-structured illumination sources of the apparatus after a given use of the elongate wand to scan an intraoral surface of a patient and before a subsequent use of the elongate wand to scan an intraoral surface of a patient.

3. The apparatus according to claim 1, wherein the probe has a transparent window through which the one or more non-structured illumination sources are configured to emit light onto an intraoral surface, and the mathematical model includes (i) a distance of a calibration target from the transparent window of the probe and (ii) Fresnel reflections from the transparent window.

4. The apparatus according to claim 1, wherein the one or more non-structured illumination sources comprise one or more broad spectrum illumination sources.

5. The apparatus according to claim 1, wherein the reflective surface is a reflective calibration target.

6. The apparatus according to claim 5, wherein the images of the reflective calibration target are acquired prior to the apparatus being packaged for commercial sale.

7. The apparatus according to claim 1, wherein the mathematical model of the non-uniform illumination from the one or more non-structured illumination sources of the apparatus includes an estimated illumination intensity-per-angle emitted from each of the one or more non-structured illumination sources.

8. The apparatus according to claim 7, wherein the estimated illumination intensity-per-angle emitted from each of the one or more non-structured illumination sources is estimated based on calibration images captured using the one or more cameras of a diffusive calibration target illuminated with the one or more non-structured illumination sources.

9. The apparatus according to claim 1, wherein the computer processor is configured to further compensate for the non-uniformity of the non-uniform illumination of the one or more non-structured illumination sources using camera-vignette calibration data indicative of a measure of relative illumination for each of the one or more cameras.

10. The apparatus according to claim 9, wherein the camera-vignette calibration data is generated by:

capturing, using the one or more cameras, calibration images of a 2D calibration target having a plurality of distinct calibration features, the capturing of the calibration images performed while the 2D calibration target is back-lit with uniform illumination, and fitting a relative illumination model to each of the one or more cameras.

11. The apparatus according to claim 9, wherein the mathematical model of the non-uniform illumination from the one or more non-structured illumination sources of the apparatus includes an estimated illumination intensity-per-angle emitted from each of the one or more non-structured illumination sources.

12. The apparatus according to claim 1, wherein the one or more non-structured illumination sources comprise one or more Near Infra-Red (NIR) illumination sources.

13. An apparatus for intraoral scanning, the apparatus comprising:

an elongate wand comprising a probe at a distal end of the elongate wand;

one or more cameras disposed within the probe;

one or more non-structured illumination sources disposed within the elongate wand, and arranged such that images of an intraoral surface are captured using the one or more cameras under non-uniform illumination from the one or more non-structured illumination sources; and a computer processor configured to analyze images captured by the one or more cameras under the non-uniform illumination from the one or more non-structured illumination sources, wherein the computer processor is configured to compensate for non-uniformity of the non-uniform illumination using calibration data indicating an amount of light received at each point (u,v) on a sensor of the one or more cameras for different respective distances from the one or more cameras, the calibration data generated by:

capturing, using the one or more cameras, calibration images of a 2D calibration target, the capturing of the calibration images performed while the 2D calibration target is disposed at a respective plurality of distances, in a given z direction in space, from the one or more cameras, and fitting a mathematical function to the calibration images, the mathematical function corresponding to an amount of light received at each point (u,v) on the sensor of the one or more cameras for each of the respective plurality of distances in the z direction.

14. The apparatus according to claim 13, wherein capturing comprises capturing calibration images of a solid-color 2D calibration target.

* * * * *